United States Patent

Girling et al.

[11] Patent Number: 5,917,417
[45] Date of Patent: Jun. 29, 1999

[54] SMOKE DETECTION SYSTEM

[76] Inventors: Christopher Girling, Bounds Cross, Shaw Green, Rushden Hertfordshire SG9 OTB; Mark Symonds, 4 Barfolds, North Mymms, Hatfield, Hertfordshire AL9 7NG; Peter David Fox, The Lodge, Stagenhoe Park, St. Pauls Walden, NR, Whitwell, Hertfordshire, SG4 8DD, all of United Kingdom

[21] Appl. No.: 08/592,404
[22] PCT Filed: Aug. 1, 1994
[86] PCT No.: PCT/GB94/01680
  § 371 Date: Jan. 30, 1996
  § 102(e) Date: Jan. 30, 1996
[87] PCT Pub. No.: WO95/04338
  PCT Pub. Date: Feb. 9, 1995

[30] Foreign Application Priority Data

Jul. 30, 1993 [GB] United Kingdom ............... 9315779

[51] Int. Cl.⁶ .................................................. G08B 17/10
[52] U.S. Cl. ........................ 340/628; 340/511; 340/577; 340/632; 250/573

[58] Field of Search ............................ 340/506, 511, 340/523, 577, 578, 579, 628, 629, 630, 632; 250/573, 574

[56] References Cited

U.S. PATENT DOCUMENTS

| | | | |
|---|---|---|---|
| 3,809,913 | 5/1974 | Prellwitz | 340/630 |
| 4,221,485 | 9/1980 | Schulze | 340/630 |
| 4,254,414 | 3/1981 | Street et al. | 340/628 |
| 4,796,205 | 1/1989 | Ishii et al. | 340/628 |
| 4,803,469 | 2/1989 | Matsushita | 340/628 |
| 4,884,222 | 11/1989 | Nagashima et al. | 340/628 |
| 5,381,130 | 1/1995 | Thuillard et al. | 340/630 |
| 5,451,931 | 9/1995 | Muller et al. | 340/630 |

*Primary Examiner*—Daniel J. Wu
*Attorney, Agent, or Firm*—Weintraub & Brady, P.C.

[57] ABSTRACT

A method of detecting the content of impurity in a gaseous medium has the steps of continually detecting impurities in the gaseous medium, emitting analyzing signals that vary with variation in impurity content, and statistically analyzing the emitted signals. When statistically analyzing the emitted signals, newer signals are accorded greater influence on outputs than are older signals, which become gradually less influential.

70 Claims, 15 Drawing Sheets

Fig. 10.
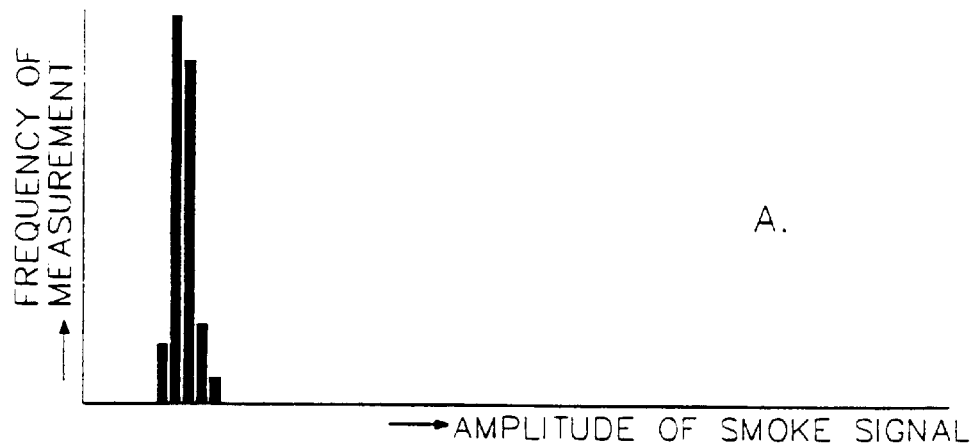
A.
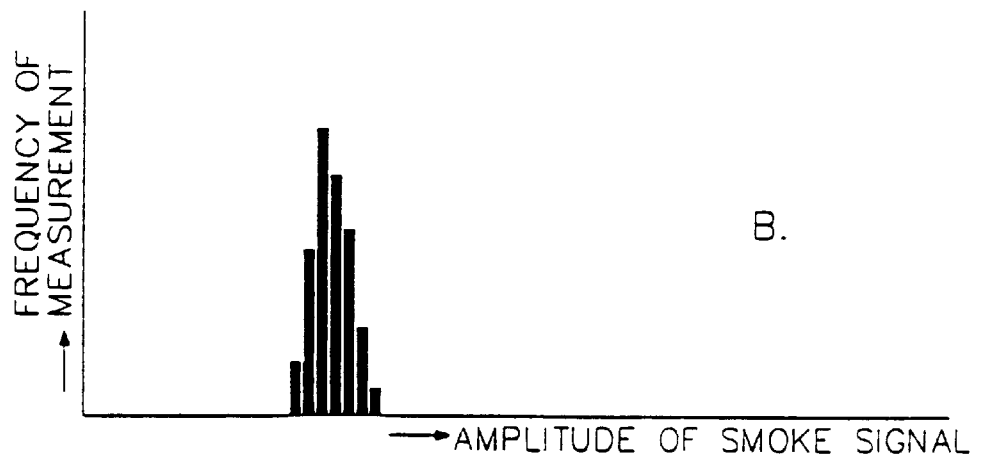
B.
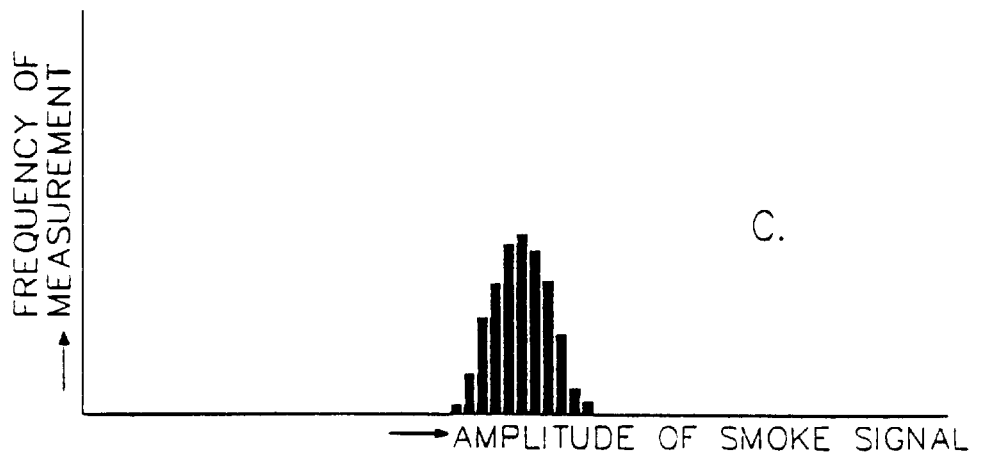
C.

SMOKE DETECTION SYSTEM

CROSS-REFERENCE TO RELATED APPLICATION

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

This invention relates to data processing apparatus and methods, and to apparatus and methods for detecting the content of impurity in a gaseous medium.

2. Prior Art

The problem of detecting a fire by means of smoke detection is not entirely solved by using a very sensitive aspirating detector.

Where high-valued property is being protected against fire, early detection of the fire is essential; allowing time for it to be tackled with the minimum of damage being caused. The build-up of a fire may be very gradual or very rapid. Electric power cable or electronic components which become overloaded result in charring or smouldering of surrounding material long before any 'red-hot' fire occurs. The cause of many fires is localised over-heating which slowly builds to a full-scale conflagration. In these cases the product of overheating is small and a high-sensitivity transducer is required to respond to it. The build-up of fire may also be seemingly instantaneous, as with an explosion. No matter which way a fire starts, early detection is essential for it to be effective and fast generation of an alarm is a normal requirement. There are two main requirements for early detection. The first is a high-sensitivity transducer by which very small amounts of the product of overheating can be detected. The second is rapid recognition that the output signal from the transducer is in fact due to the product of overheating and not a signal which could be generated from any other source. Basically, a detector consists of a transducer giving a signal proportional to the product of overheating and a device for giving an output signal when the transducer output signal has reached a given alarm level. The general environment for a detector is one where a considerable variation of signal from a high-sensitivity transducer will be normal. High sensitivity alone will either produce a fire signal due to this normal background activity or the given alarm level must be raised to a point where the normal background activity will be ignored, thus de-sensitising the detector. This places a practical limit on the sensitivity of the detector.

In order to prevent the internal parts of a transducer from becoming contaminated, an air filter is employed to remove larger particles than anticipated with products of overheating materials. The performance and renewal of this filter, with known aspirating detectors, is often a problem in maintaining a consistent performance by a detector. The problem arises in that, as the air filter becomes increasingly contaminated through usage, the effective pore size of filter medium becomes increasingly smaller. This effect is sometimes known as "tea leafing" because of the similarity with the effect of tea leaves hindering passage of tea when a tea strainer is used. The effect on conventional aspirating smoke detectors is that the sensitivity of the detector decays with time as the filter becomes increasingly blocked, leaving the system in some cases significantly less sensitive after only a few months of use.

Furthermore, in existing aspirating smoke detection systems, it is desirable that the rate of air flow down the sampling pipes is at a maximum, because this minimises response time to fire situations. By reason of the high rate of flow down the sampling pipes, it is also likely that significant amounts of pollution other than smoke and having the aforementioned tendency to block filters will be drawn into the detector. "Referencing" is the process by which an air pollution transducer of an air pollution detection unit samples the air entering a protected volume and provides an offset signal to other air pollution detection units within the volume. The intention of referencing is to avoid the problem of pollution entering the volume from outside causing an alarm. There are two possible roles for the air pollution detection unit in referencing. The first is to provide a reference signal and the unit is called a reference unit; the second is to provide acceptance for a reference signal and the unit is called a detector unit. "Referencing" is generally applied in circumstances where the unpurified external atmosphere has access to the protected volume, for example via ducting or a window. It is not needed in circumstances where the external atmosphere does not have access to the volume or is purified before it reaches the volume.

BRIEF SUMMARY OF THE INVENTION

According to a first aspect of the present invention, there is provided a method of detecting the content of impurity in a gaseous medium, comprising continually statistically analysing signals which are emitted by detecting means detecting said impurity and which vary with variation in said content, characterised in that, in the statistical analysis, newer signals are accorded greater influence on outputs than are older signals, which become gradually less influential.

According to a second aspect of the present invention, there is provided apparatus for detecting the content of impurity in a gaseous medium, comprising detecting means serving to detect said impurity, analysing means serving continually to analyse statistically signals which are emitted by said detecting means and which vary with variation in said content, said analysing means comprising numerically calculating means, characterised in that said numerically calculating means continually performs a statistical analysis in which newer data inputs are accorded greater influence on the outputs than are older data inputs, which become gradually less influential.

Owing to these two aspects of the present invention, it is possible to provide a continuous statistical analysis in respect of a continuously advancing time period of constant duration, in such manner as to obtain the general trend of any series of measurements of the impurity content, while not giving undue significance to any single measurement that is considerably outside the general trend.

According to a third aspect of the present invention, there is provided a data processing method utilizing numerical calculation, wherein a statistical analysis is continually performed in which newer data inputs are accorded greater influence on the outputs than are older data inputs, which become gradually less influential, characterised by sorting said newer data inputs into a plurality of classes into which the older data inputs have already been sorted, and incrementing each class into which such newer data input is sorted by an amount dependent upon the existing entry in that class and decrementing the classes into which such newer data input is not sorted by amounts dependent upon the respective existing entries in those classes.

According to a fourth aspect of the present invention, there is provided data processing apparatus incorporating numerically calculating means such that a statistical analysis can be continually performed in which newer data inputs are accorded greater influence on the outputs than are older data inputs, which become gradually less influential, characterised in that said calculating means sorts said newer data inputs into a plurality of classes into which said calculating means has already sorted the older data inputs, and in that said calculating means increments each class into which such newer data input is sorted by an amount dependent upon the existing entry in that class and decrements the classes into which such newer data input is not sorted by amounts dependent upon the respective existing entries in those classes.

Owing to these two aspects of the invention, it is possible to provide a continuous statistical analysis, in respect of a continuously advancing time period of constant duration, of a considerable quantity of data in a small memory bank, which can be continually applicable over a continuous time to the present time. These aspects of the invention have a wide variety of industrial applications, not only the detection of pmpurity in a gaseous medium.

According to a fifth aspect of the present invention, there is provided a method of detecting the content of impurity in a gaseous medium, comprising receiving signals which are emitted by detecting means detecting said impurity and which vary with variation in said content, and producing a warning indication if and when amplitude of the signals passes an abnormal threshold, characterised by continually statistically analysing the received signals to set said abnormal threshold.

According to a sixth aspect of the present invention, there is provided apparatus for detecting the content of impurity in a gaseous medium, comprising detecting means serving to detect said impurity, receiving means serving to receive signals which are emitted by said detecting means and which vary with variation in said content, and warning-producing means serving to produce a warning indication if and when amplitude of the signals passes an abnormal threshold, characterised by continually statistically analysing means interposed between said receiving means and said warning-producing means and which continually statistically analyse the received signals to set said abnormal threshold.

Owing to these two aspects of the invention it is possible to set thresholds more sensitively.

According to a seventh aspect of the present invention, there is provided a method of detecting the content of impurity in a gaseous medium, comprising receiving signals which are emitted by detecting means detecting said impurity and which vary with variation in said content, and producing a warning indication if and when amplitude of the signals passes an abnormal threshold, characterised by continually statistically analysing the received signals to ascertain when a centre of distribution of amplitude of the signals passes said threshold and producing said warning indication accordingly.

According to an eighth aspect of the present invention, there is provided apparatus for detecting the content of impurity in a gaseous medium, comprising detecting means serving to detect said impurity, receiving means serving to receive signals which are emitted by said detecting means and which vary with variation in said content, and warning-producing means serving to produce a warning indication if and when amplitude of the signals passes an abnormal threshold, characterised by continually statistically analysing means interposed between said receiving means and said warning-producing means and which continually statistically analyse the received signals to ascertain when a centre of distribution of amplitude of the signals passes said abnormal threshold.

Owing to these two aspects of the invention, it is possible to be more certain that a series of measurements constitutes a true signal beyond the threshold.

The warning-producing means may produce a warning indication if and when the amplitude of one or more individual signals is abnormally different relative to an ordinary distribution of the signals and/or if and when a centre of distribution of the amplitude of the signals changes to an abnormal value. The centre of distribution may be represented by, for example, the mode, the median or the mean.

These possibilities have the advantage of warning of a fire situation or an abnormal event in the apparatus, for example an operational fault in the detecting means or in a filter upstream of the detecting means.

According to a ninth aspect of the present invention, there is provided a detector for detecting impurity in a gaseous medium, comprising a housing, an inlet of said housing for entry of said gaseous medium carrying said impurity, radiation-emitting means for emitting a beam of radiation to pass through said medium and focussed to a first location in said housing, radiation-reflective means for focussing radiation scattered from said beam by said impurity to a second location in the housing, and radiation-sensing means disposed at said second location for sensing the radiation focussed thereto by said radiation-reflective means, characterised in that said radiation-reflective means is disposed opposite said radiation-emitting means and encircles said first location and in that said second location is in the region of said radiation-emitting means.

An advantage of this aspect of the invention is that the radiation-sensing means detects radiation scattered at relatively small angles to the beam, at which angles the majority of radiation is scattered in practice, whereby the detector can be more sensitive for a given operating energy supplied to the detector.

According to a tenth aspect of the present invention, there is provided a method of detecting the content of impurity in a stream of gaseous medium flowing through main duct means, characterised by causing only part of said stream to flow into secondary duct means and detecting the content of the impurity in the gaseous medium in said secondary duct means.

According to an eleventh aspect of the present invention, there is provided apparatus for detecting the content of impurity in a stream of gaseous medium, comprising main duct means through which said stream can flow, secondary duct means communicating with said main duct means for receiving only part of said stream, and detecting means serving to detect the content of the impurity in the gaseous medium in said secondary duct means.

Owing to these two aspects of the present invention, the response time of the detecting means to the content of impurity entering the main duct means need not be dependent upon the throughflow cross-sectional area of a detection chamber and, moreover, the detecting means is not exposed to all of the impurity flowing through the main duct means, whereby the service life of the detecting means may be improved.

The present invention is applicable to detection of a variety of impurities, for example to the detection of particulate impurities, such as smoke, or gaseous impurities, such as methane, in a gaseous medium, particularly air.

According to a twelfth aspect of the present invention, there is provided a method of detecting the speed of a stream of gaseous medium, comprising passing the medium over an electrically heated sensor, thereby tending to cool said sensor from a desired temperature, characterised by increasing the electrical power dissipated in said sensor to counterbalance the cooling tendency, and measuring the increase in the electrical power dissipated.

According to a thirteenth aspect of the present invention, there is provided apparatus for detecting the speed of a stream of gaseous medium, comprising an electrically heatable sensor, and electrical power supply means connected to said sensor for heating the sensor, characterised by control means connected to said supply means and said sensor and serving to cause increase of electrical power dissipated in said sensor to counterbalance cooling of said sensor, and measuring means serving to measure said increase of electrical power dissipated.

Owing to these two aspects of the invention, the desired temperature need not be set at more than a few degrees Kelvin above the temperature of the ambient stream.

In order that the invention may be clearly understood and readily carried into effect, reference will now be made, by way of example, to the accompanying drawings, in which:

BRIEF DESCRIPTION OF THE SEVERAL VIEWS OF THE DRAWING

FIGS. 10A to 10C are diagrams corresponding to FIG. 9, but illustrating respective possible histograms representing respective different general smoke levels.

DETAILED DESCRIPTION OF THE INVENTION

Figure 1:
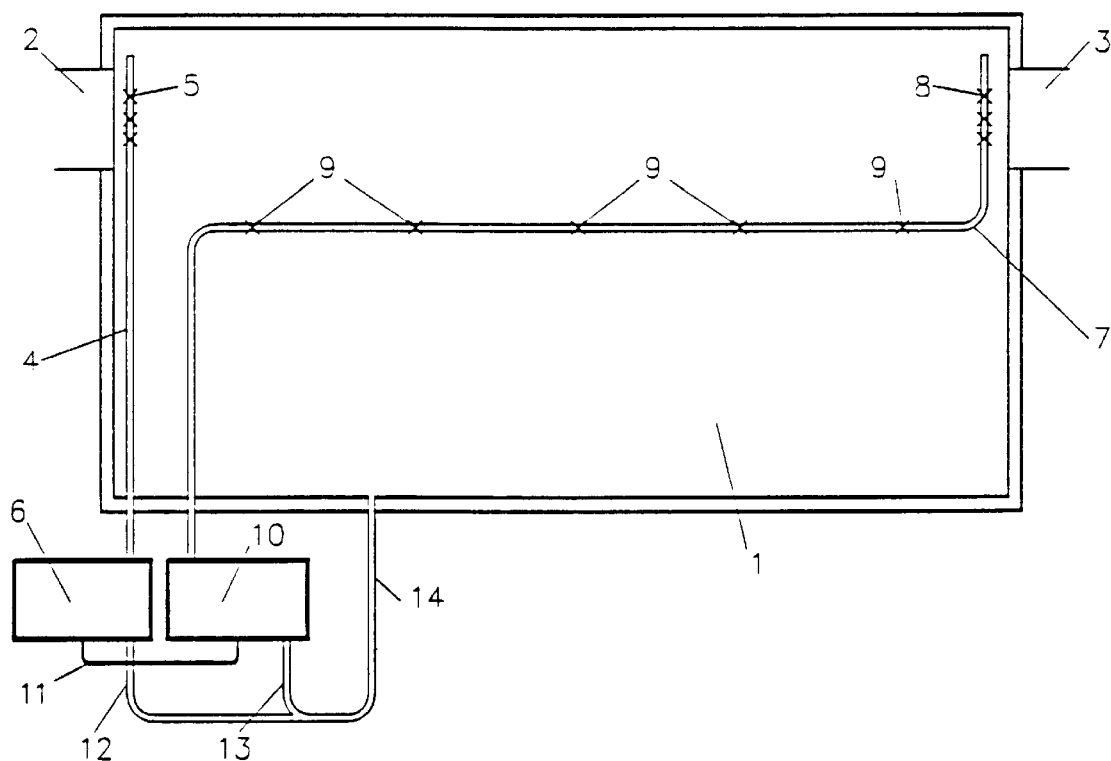
FIG. 1 is a diagram of a smoke detection system installed in an air-conditioned room of a building.

Referring to FIG. 1, a room 1 constituting a volume to be protected against fire has a fresh air inlet 2 and an air outlet 3. Reference sampling ducting 4 having sampling holes 5 at the exit from the fresh air inlet 2 leads to a reference module 6, whilst smoke detection sampling ducting 7 having sampling holes 8 at the entry to the air outlet 3 and sampling holes 9 distributed along the room, extends to a smoke detection module 10 electrically interconnected with the module 6 by a cable 11. Respective air return ductings 12 and 13 lead from the modules 6 and 10 to common return ducting 14 leading back to the room 1, as shown, or to exhaust.

Figure 2:
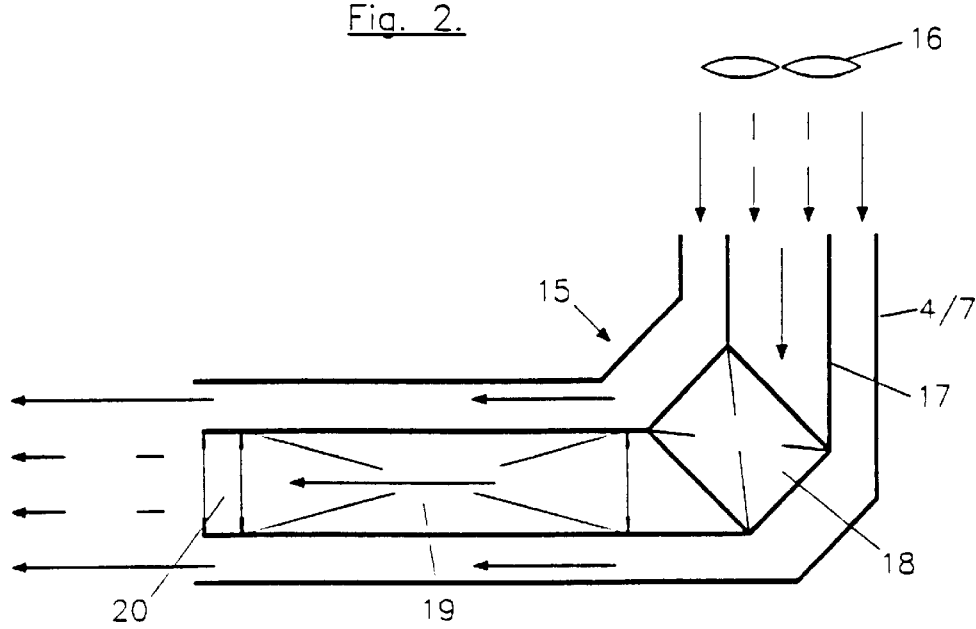
FIG. 2 shows one of two identical sampling arrangements forming respective parts of a reference module and a detection module shown in FIG. 1.

Referring to FIG. 2, each module 6 or 10 contains a sampling arrangement 15 included in the reference sampling ducting 4 or the detection sampling ducting 7. The ducting 4 or 7 contains a fan 16 which draws air from the room 1 and forces it through the ducting, which contains a co-axial duct 17, which itself contains a filter 18, a detector head 19 downstream of the filter and an air-speed transducer 20 downstream of the detector head 19.

With this simple bypass arrangement, as the air stream is forced into the duct 17 containing the smoke detector head 19, a large proportion of the air is vented to atmosphere or to the air return flow, without entering the filter 18 and thus the detector 19 and the air-speed transducer 20 downstream of the filter. This leaves only a smaller, representative sample of the air to pass through the filter 18 and then the detector 19 and the transducer 20. This has the advantages that the maximum speed of flow down the sampling ducting 4 or 5 is obtained in order particularly to minimise response time of the detector unit to a fire situation, and that, as only a small percentage of the potentially contaminating airflow is passed through the filter 18, the filter, detector head and transducer service lives are increased.

Figure 3:
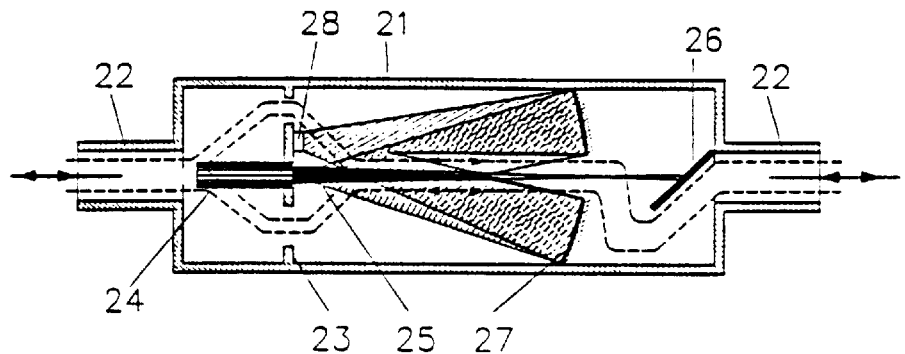
FIG. 3 shows an axial section through a detector head included in the sampling arrangement of FIG. 2, FIGS. 4 and 5 show respectively a plan view and an elevation of an air-speed transducer of FIG. 2.

Referring to FIG. 3, the smoke detector head 19 includes a tubular housing 21 formed with axial air inlets/outlets 22 and provided internally with an apertured diametral partition 23 upon which is mounted co-axially a focussed light source 24, such as a semiconductor optical emitter, to illuminate a sampling air stream from the protected volume 1. The light source 24 is focussed to a beam 25 which passes through the sampling air stream. Light which is not scattered by matter in the air stream enters a light trap 26 through the middle of an annular concave mirror 27 in order to prevent it from reaching a light sensor 28 mounted upon the partition 23. The mirror 27 encircles the focus region of the beam 25 and is peripherally sealed to the inside surface of the housing to force the air stream to pass through the focus region. The arrangement of the inlets/outlets 22 axially of the housing 21 also promotes generally axial flow of the air stream through the housing. Light which is scattered within a few degrees of the forward direction of the light source 24 strikes the face of the concave mirror 27 which reflects it back to the light sensor 28 mounted near the light source 24. The light scattered from the mass of the sample within the depth of focus of the mirror 27 is thus detected. The detector head 19 can be used in a reference unit or in a detector unit.

Figure 4:
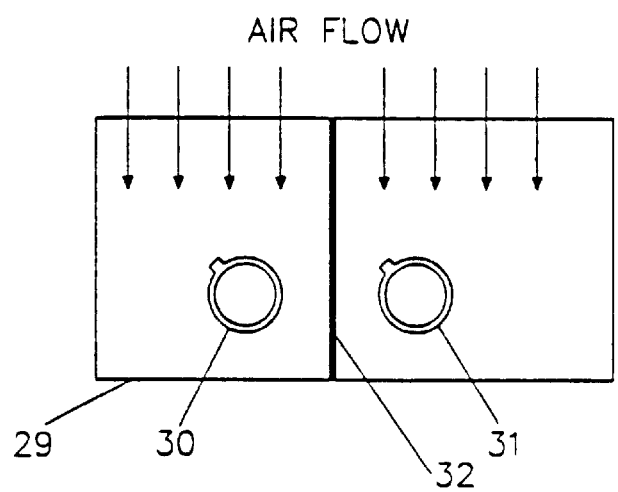
Figure 5:
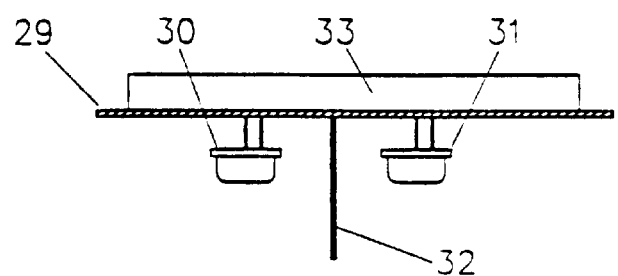

Referring to FIGS. 4 and 5, the air-speed transducer includes a printed circuit board 29 to one side of which are mounted an air-speed sensor 30 and a reference sensor 31 separated by a heat screen 32, other components of its electrical circuitry being mounted upon the reverse side of the printed circuit board, as indicated at 33.

Figure 6:
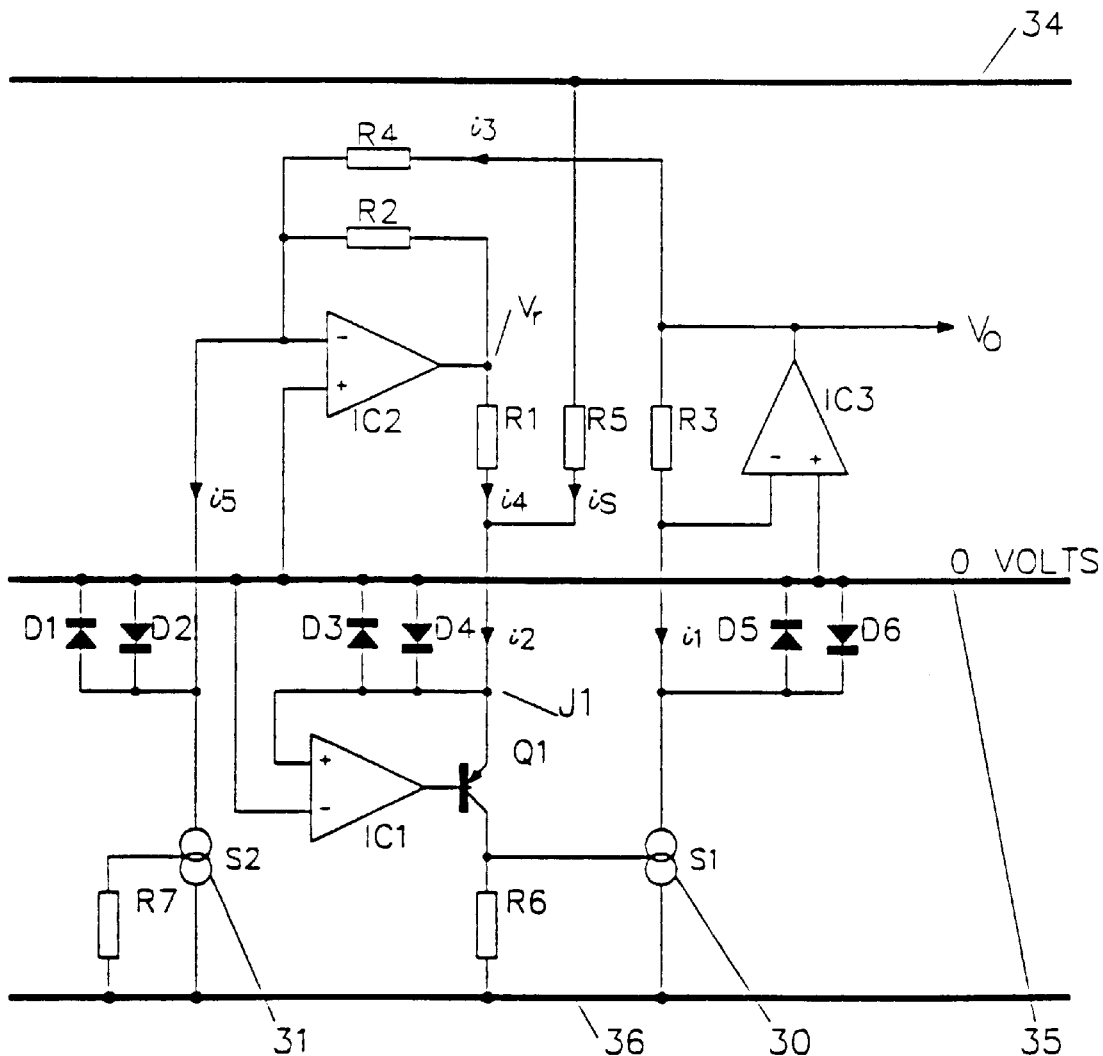
FIG. 6 shows a diagram of electrical circuitry of the transducer of FIGS. 4 and 5.
Figure 7A:
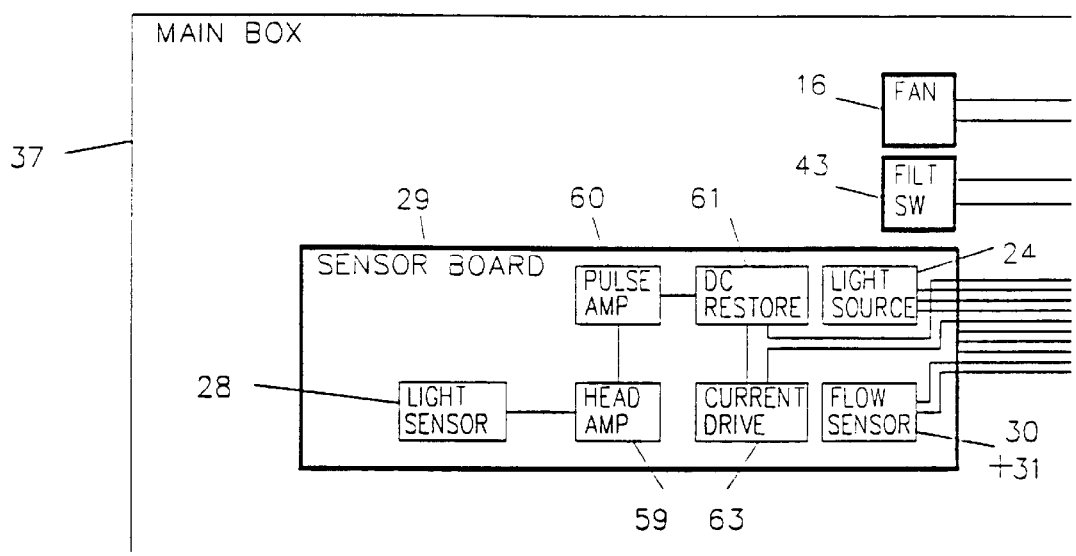
FIG. 7 shows a block diagram of electrical functions of the detection module.
Figure 7B:
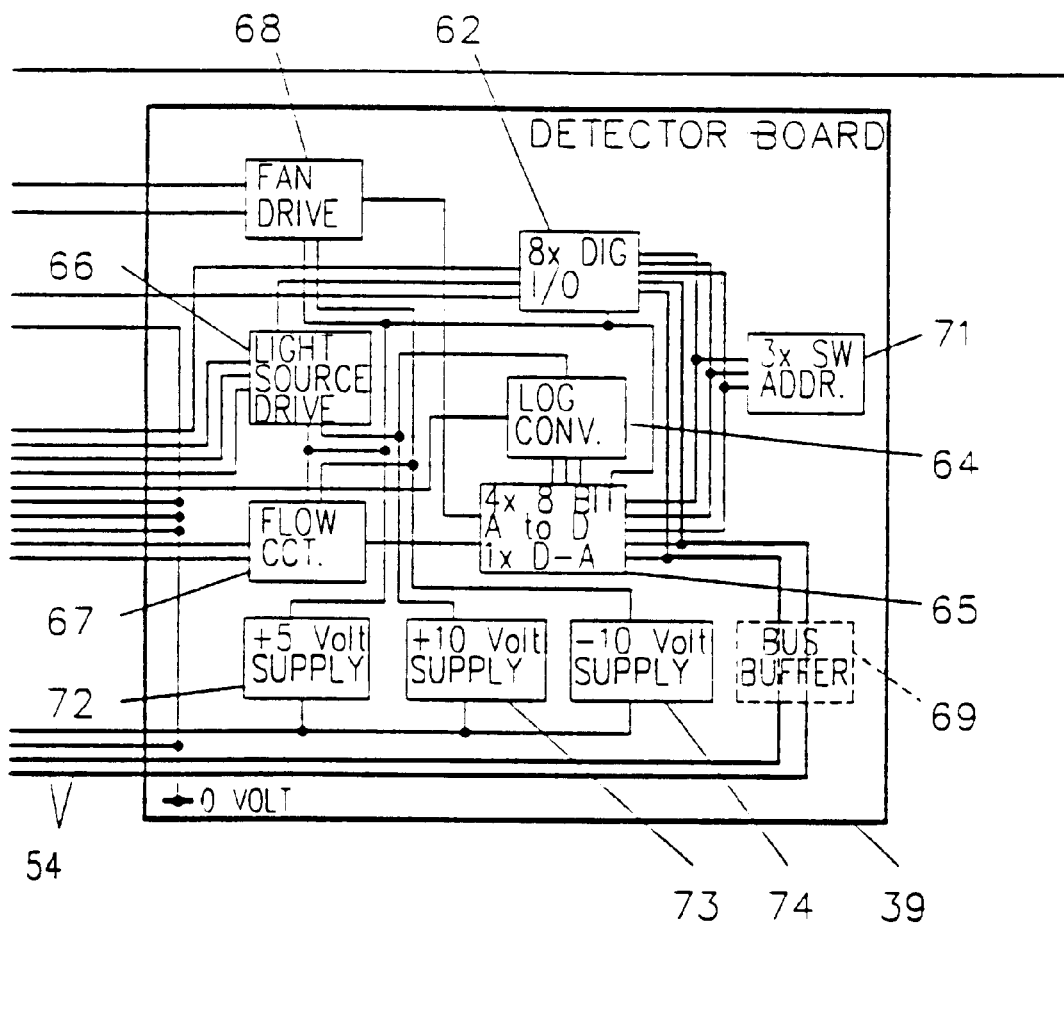
Figure 7C:
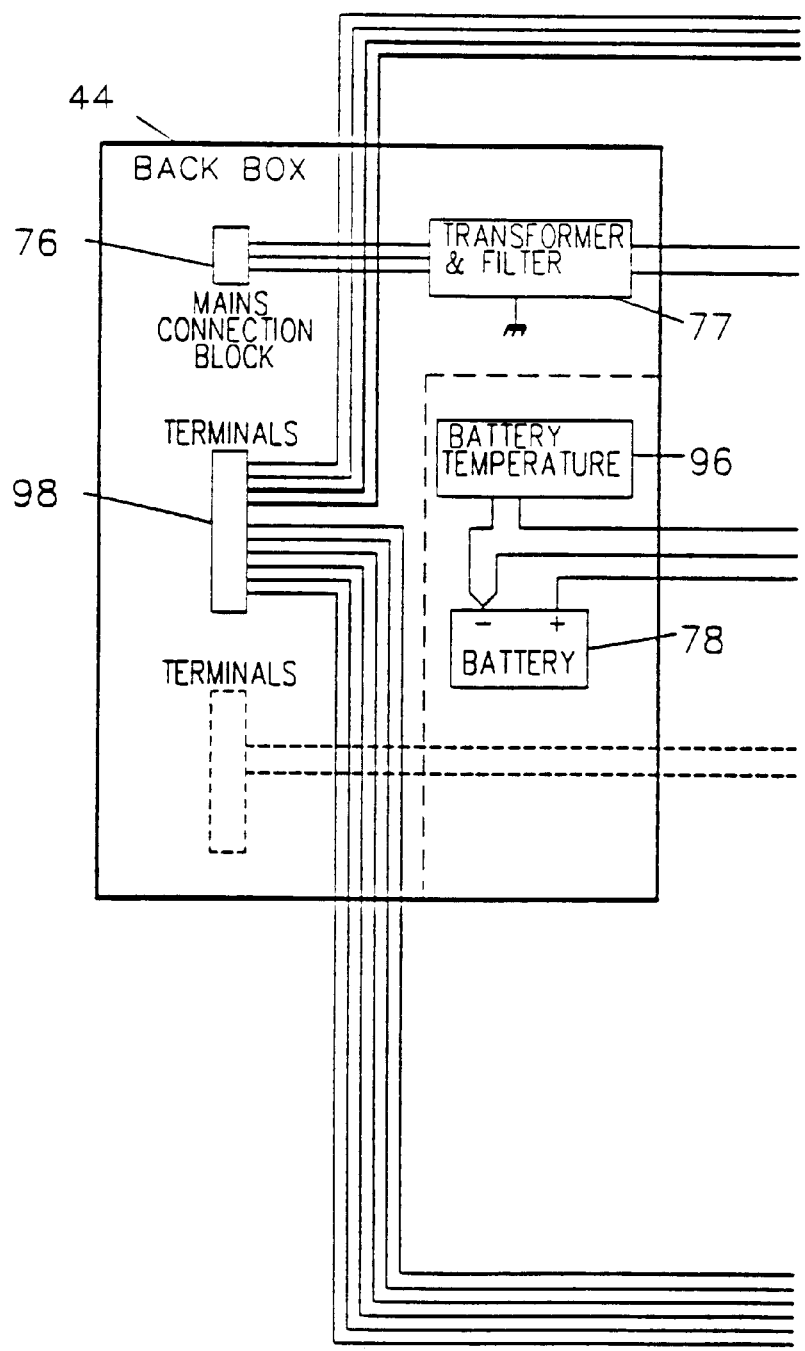
Figure 7D:
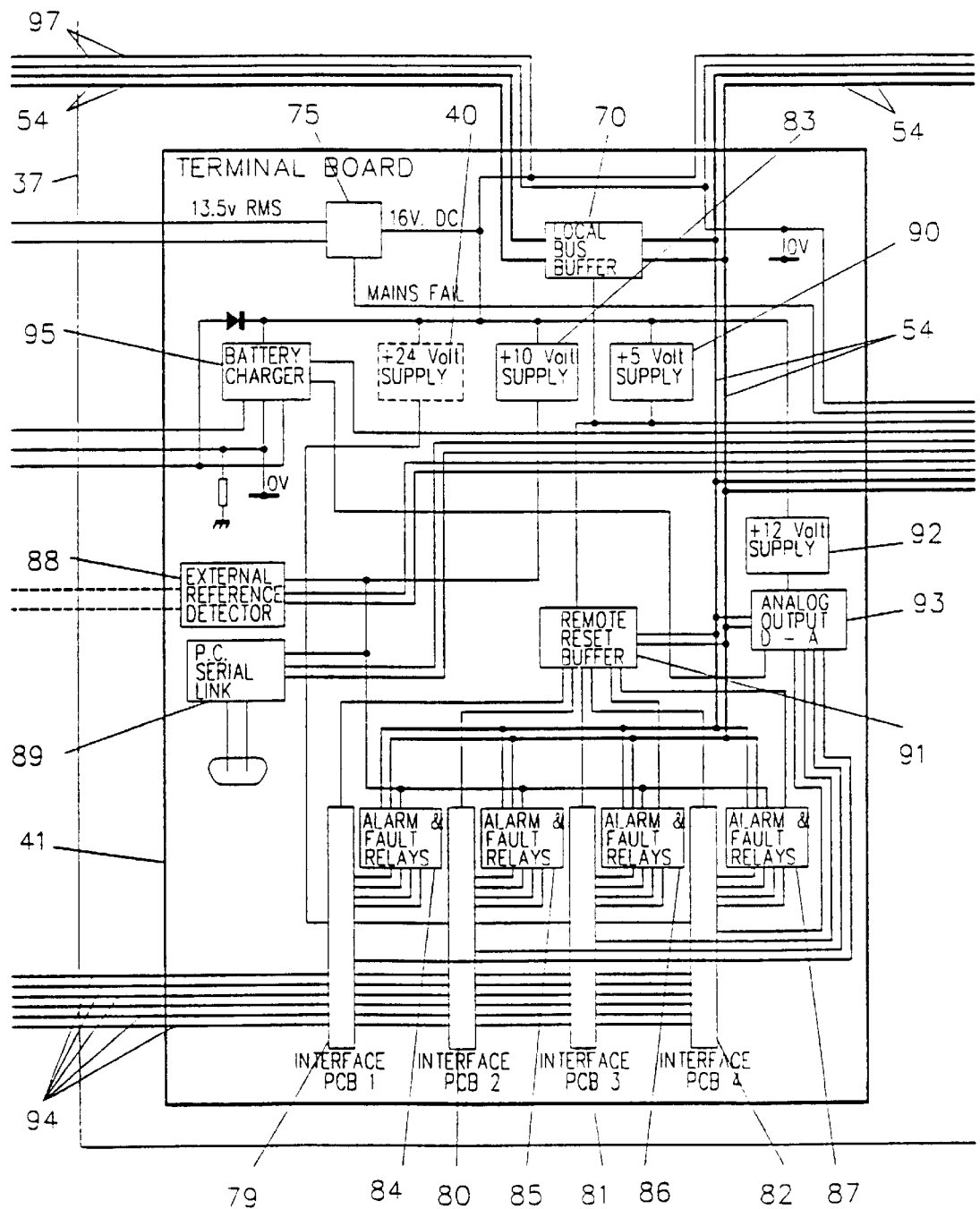
Figure 7E:
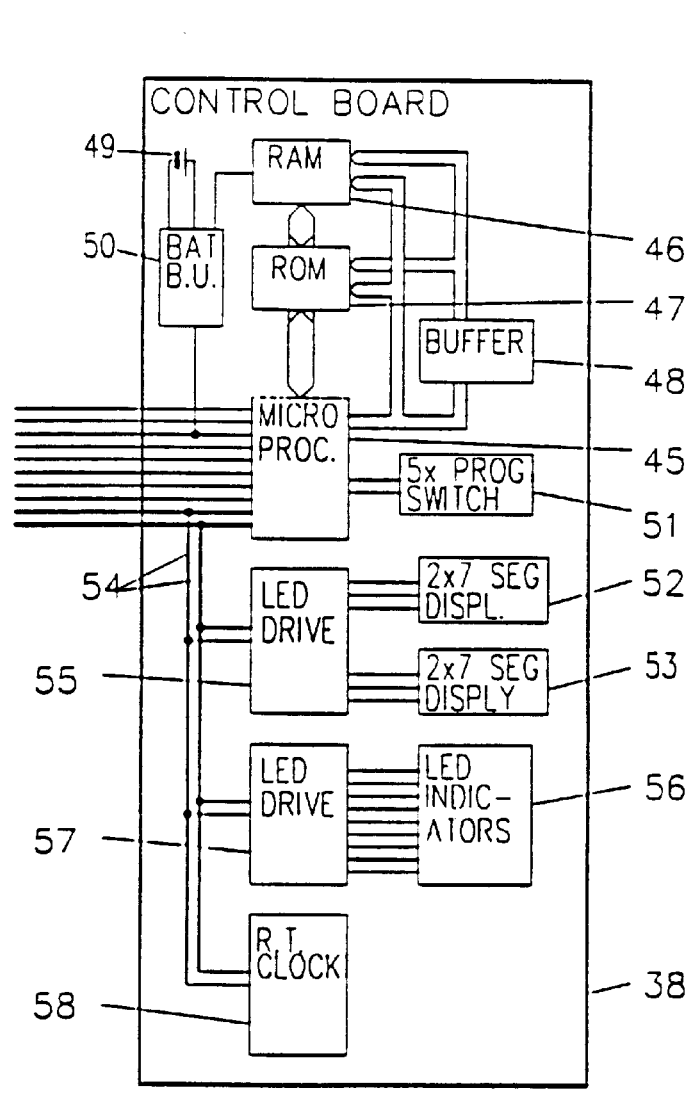

Referring to FIG. 6, the diagram shows the sensors 30 and 31 as S1 and S2, respectively, the respective currents through which are set by resistors R6 and R7 such that the current that would be set by R6 is at least several times the current $i_5$ which is set in S2 (i.e. the resistance of R7 is at least several times that of R6). The current $i_1$ which actually flows through S1 is the current which is set by R6 minus the current $i_2$ flowing through a transistor Q1. $i_2$ is $i_4$ (that is the difference between the current $i_5$ and the current $i_3$) plus a constant current $i_s$. A positive potential is applied across a resistor R5 by a positive D.C. supply line 34 to produce the current $i_s$. A junction J1 is maintained at zero volts by an integrated circuit IC1 which acts as a driver for the transistor Q1. An integrated circuit IC2 inverts and amplifies the current in S2, in co-operation with the resistors R1, R2 and R4. An integrated circuit IC3, in co-operation with the resistor R3 converts the current $i_1$ in S1 into an output voltage $V_0$. Diodes D1 to D6 protect the integrated circuits IC1 to IC3 in relation to a zero volt line 34. A negative D.C. supply line 36 establishes control voltages in S1 and S2.

Each of the sensors 30 and 31 is, for example, an integrated circuit device LM334 available from National Semiconductor Limited and is chosen because it can dissipate enough power to raise its own temperature in a cooling air flow. The circuitry of FIG. 6 measures the additional power required to maintain a constant temperature rise, above the ambient temperature, of the sensor 30 while it is being cooled in the air flow. It is assumed that the air speed is directly proportional to the additional power required. The ambient temperature is measured in order to achieve the comparison, so that the reference sensor 31 is provided. The reference sensor 31 is operated with a very low power dissipation, in the same air speed as the sensor 30, and thus acts as a reference. Owing to its very low power dissipation, its temperature rise above ambient temperature is negligible and thus any cooling effect is negligible. To ensure that heat from the detection sensor 30 does not affect the temperature of the reference sensor 31, the heat screen 32 is provided to guard against thermal transfer by convention and radiation. As an example, the circuitry can be designed to maintain the temperature of the detection sensor 30 at 5° Kelvin above the ambient temperature.

The voltage $V_o$ is proportional to the current flowing in S1, which is proportional to the inverse of the effective thermal impedance Z of S1 and hence proportional to the air speed. Its mathematical derivation now follows. The circuitry is configured such that:

$$i_2 = i_4 + i_s$$

$$i_3 = i_1/A$$

(where $A = R7/R6 = R4/R3 = R2/R1$)

$$i_4 = A.i_5 - i_1$$

(where $i_5 = K_r.T_a$)

(where $K_r$ is a constant set by R7 and $T_a$ is the ambient temperature in °Kelvin),
from which can be derived $i_1 = K.(T_a + dT)(A.K_r.T_a + i_s - i_1)$
(where dT=temperature rise of the sensor 30 due to its own power dissipation$=i_1.V.Z$);
if $K = A.K_r$, by design, then:

$$K.dT = i_s \text{ or } dT = i_s/K$$

therefore, $i_1.V.Z. = i_s/K$ or $i_1 = I_s/K.V.Z.$
therefore, $V_o = R_3.i_1 = R_3.i_s/K.V.Z.$ The limit of the latter function occurs when $i_4 = -i_s$, because the current through the transistor Q1 cannot be negative.

The advantages of the air-speed transducer 20 are that the ambient temperature is measured in the same air stream as the air speed, the components may be standard and thus easily obtained without special selection and without requiring special processing, low air speeds may be adequately measured for the present purpose without requiring special setting-up calibrations, for example in the event of needing to replace one or other of the sensors 30 and 31, and the temperature of the sensor 30 need not be raised any more than 5° Kelvin above ambient temperature, so allowing it to be used in Intrinsically Safe Environments (i.e. environments where safety is at a premium).

Referring to FIG. 7, the electrical functions of the detection module 10 are housed chiefly in a main box 37 which contains a control board 38, a detector board 39, the sensor board 29, a terminal board 41, a fan 16 and a filter switch 43. There is also a back box 44. The control board 38 includes a microprocessor 45 which enters and processes data in a RAM 46 in a manner determined by the software programme stored in the ROM 47. A buffer 48 aids in addressing the large quantity of data in the RAM 46. The contents of the RAM 46 are protected against erasure through loss of power, by means of a back-up battery 49 on the control board 38 and a management circuit 50.

Variables which may be arbitrarily set on installation of the detection module 10 may be entered by means of programming switches 51 in conjunction with four 7-segment displays 52 and 53. These variables are entered in the RAM 46 via the microprocessor 45 and the references for the variables are displayed by the 7-segment displays 52 while the values of the variables are displayed by the 7-segment displays 53. The actual numbers displayed by the 7-segment displays 52 and 53 are controlled by the microprocessor 45 by means of data transmitted down local bus lines 54 which is translated by an LED driver 55.

LEDs 56 are switched on or off in order to indicate the various fault and alarm conditions which the microprocessor 45 has detected. This data is received via the bus lines 54 and translated by an LED driver 57. A real time clock circuit 58 keeps track of the date and time for use in maintaining a log of events in the RAM 46 as determined by the microprocessor 45.

The board 29 is mounted within the detector head 19 in order to keep short electrical leads connecting the same to the light sensor 28 and the sensors 30 and 31, so as to keep those leads comparatively free from the pick-up of electrical interference to which they are particularly sensitive. The light sensor 28 gives a small signal current pulse proportional to the amount of scattered light. This current is translated to a voltage by a head amplifier 59 and the pulse is amplified by a pulse amplifier 60. The D.C. level of the signal pulse is restored by a D.C. restore circuit 61 which obtains the data necessary from the microprocessor 45 via the bus lines 54 and an eight-bit remote digital input/output circuit 62 on the detector board 39. A current pulse proportional to the resulting signal pulse is generated by a current drive circuit 63. The current signal pulse is fed to a log converter 64 on the detector board 39 and giving an output voltage proportional to the logarithm of the input current. The output of the log converter 64 is dependent upon the temperature of its elements and a reference current set up within it. These three quantities are represented by voltages within it and are communicated to the microprocessor 45. These three signals from the log converter 64 are converted to digital quantities by means of three of four analogue-to-digital converters contained in a circuit 65. The resulting digital data is sent to the microprocessor 45 via the bus lines 54. The light source 24 is an LED which is driven and monitored by a light source drive circuit 66. The circuit 66 triggers the light source to give short pulses of light as determined by the microprocessor 45 via the bus lines 54 and the input/output circuit 62. The flow sensors 30 and 31 in conjunction with a flow circuit 67 produce a voltage proportional to the air speed through the detector head 19. This signal is converted to a digital quantity by the fourth of the analogue-to-digital converters contained in the circuit 65 and the data produced is sent to the microprocessor 45 via the bus lines 54.

Figure 8:
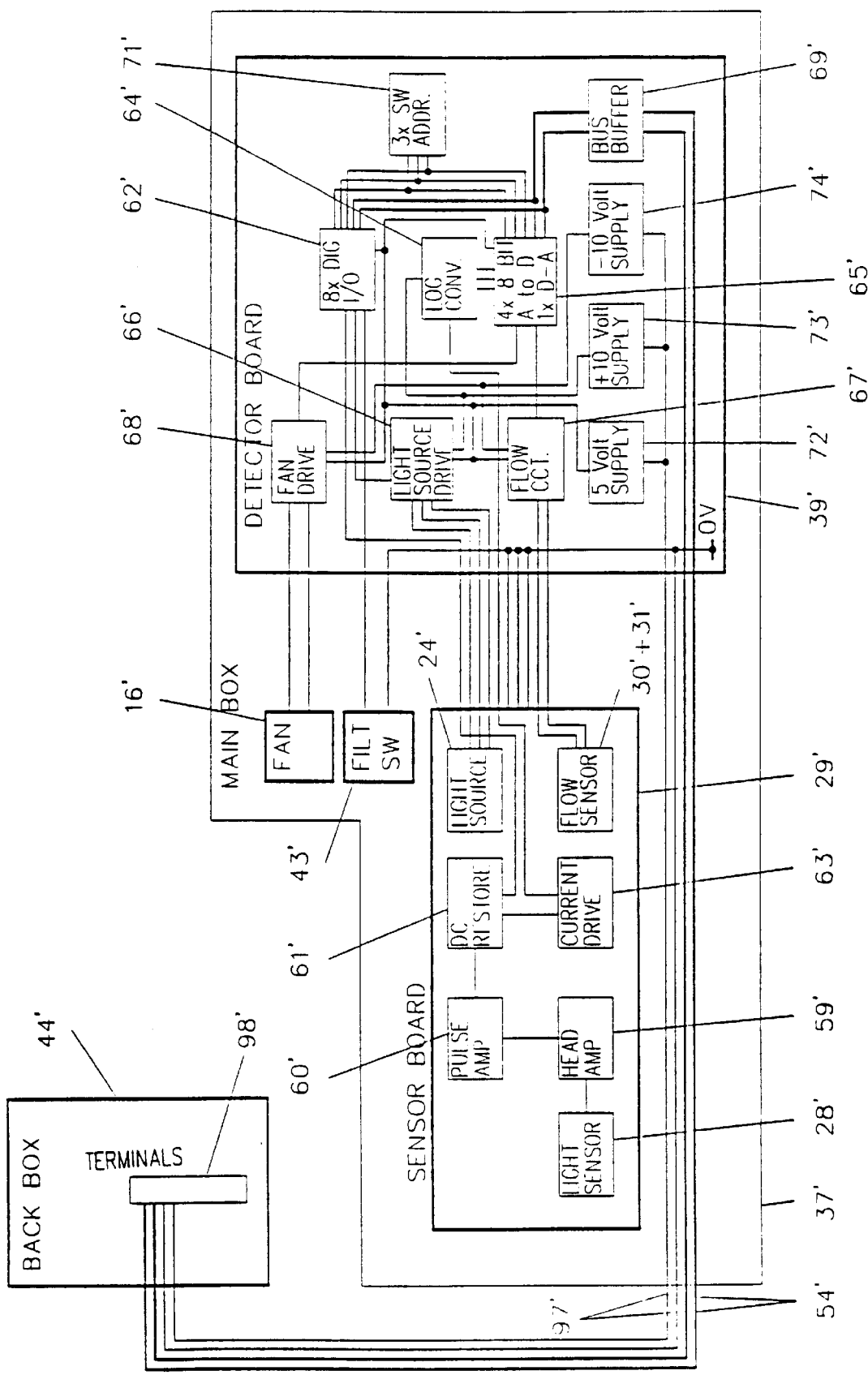
FIG. 8 shows a block diagram of electrical functions of a slave module forming either a slave detection module or the reference module.

The fan 16 drives air through the sampling ducting 7 and the detector head 19. The speed at which it does so is controlled by the microprocessor 45 via the bus lines 54 and the circuit 65. This produces an analogue voltage level which controls a drive 68 for the fan 16. Under certain circumstances, the bus lines 54 may work through a bus buffer 69 to enable communication along lengthy bus lines. Under other circumstances, this function is performed by a local bus buffer 70 on the terminal board 41. The circuits 62 and 65 have a special address for recognition on the local bus lines 54, and this address can be sent by a group of three switches 71. The +5 volt supply, +10 volt supply and −10 volt supply required for operating the circuitry are derived from respective regulators 72 to 74. The regulators 72 to 74 obtain their own supply from a 16 volt D.C. output rectifier 75 on the terminal board 41. The rectifier 75 is connected to a mains connection block 76 in the back box 44 by way of a transformer and filter circuit 77. The rectifier 75 has an output voltage which will fall to zero if the mains supply fails and a corresponding signal is fed directly to the microprocessor 45 to show a false condition and switch over to supply from a battery 78. The 16 volt output from the rectifier is also used to supply a +24 volts regulator 40 connected to four interface printed circuit boards 79 to 82. The 16 volt output is also used to a +10 volt supply regulator 83 connected to alarm and fault relays 84 to 87 associated with the respective interfaces 79 to 82. The regulator 83 also supplies a serial interface to a driver 88 and a serial interface of a personal computer serial link 89. The rectifier 75 also supplies a +5 volt regulator 90 which supplies the microprocessor 45, the local bus buffer 70 and a remote reset buffer 91. The rectifier 75 further supplies a +12 volt regulator 92 specifically for supplying an analogue output digital-to-analogue converter 93. The converter 93 provides an analogue representation of the respective outputs from four detector heads, which serve to detect smoke in respective rooms in a building, one of the rooms being referenced 1 and the sensor board and the detector board relating to that particular detector head being referenced 29 and 39. The other detector heads, sensor boards and detector boards are simply duplicates and are contained in slave modules each as shown in FIG. 8. The respective outputs from the converter 93 are fed to the PCBs 79 to 82 which are associated with the respective four detector heads. The alarm and fault relays 84 to 87 produce voltage-free switching action onto the connectors to the PCBs 79 to 82, respectively. The data for switching of the relays is communicated via the bus lines 54 from the microprocessor 45. The microprocessor 45 can be reset, in the event of its failure, by means of an output from the remote reset buffer 91, which receives inputs directly from the respective PCBs 79 to 82. Similarly, the alarm and fault relays 84 to 87 for each of the PCBs 79 to 82 may be taken out of a latched condition. Six lines 94 are taken from the PCBs 79 to 82 to terminate in the back box 44 to allow configuration of circuitry between the alarm and fault relay contacts, the remote reset input and the output from the converter 93, to whatever bus conditions are required on these six lines. The battery 78 has a charger 95 which is supplied from the rectifier 75 and the charge rate of which is controlled in accordance with temperature as sensed by a temperature sensor 96 beside the battery 78. A battery test circuit is included in the charger 95 and receives instructions to test the battery 78 from the microprocessor 45 via the bus lines 54 and the converter 93. The results of this test are communicated back to the microprocessor 45. A personal computer (not shown) and the microprocessor 45 may intercommunicate by way of the serial link 89, in order to permit entering of the different variables which may be arbitrarily set in the microprocessor 45; also, it allows the microprocessor to interact with a software programme on the personal computer and demonstrate graphically the functioning of the microprocessor as it monitors the four detection modules associated with the respective rooms. In addition to the local bus lines 54 which carry the data, there are two local bus lines 97 which are connected to terminals in the back box 44 in the same manner as the lines 54, but which act as power supply lines. The lines 54 and 97 facilitate communication with the other three detection modules 10. If the reference module 6 is required to be used with the four detector modules, then it also can be connected into the bus lines 54 and 97. If a reference module so connected is required to serve more than the four detection modules provided for in FIG. 7, then another "master" unit according to FIG. 7 can be connected via terminals 98 in the back box 44 to the external driver 88.

Referring to FIG. 8, the corresponding, identical parts to those shown in FIG. 7 are given the same reference numerals, but primed. It will be noted that the bus buffer 69' is now always required.

Not only does the back box 44 or 44' take all of the electrical terminations, but also it takes all of the air sampling ducting terminations; this feature has the advantage that the main box 37 or 37' does not need to be brought to site until the electrical and air sampling installations have been completed and the back box 44 or 44' connected up, whereafter the main box 37 or 37' can simply be brought on site and plugged into the back box. This minimizes the risk of theft of, damage to, or interference with, the main box 37 or 37'.

The apparatus as so far described provides means of recognising a true, i.e. smoke, signal which means will allow the given alarm level to be lower and thus the apparatus will be able to take fuller advantage of the high-sensitivity detector head 19.

The recognition of a true signal is achieved as follows. The signal from the high-sensitivity smoke detector head 19 is sampled at given intervals, say once a second, then, after an initialisation time period, the distribution of readings is statistically analysed in the suitably programmed microprocessor 45. A mean and a standard deviation of the signal level are calculated assuming that that distribution is a normal distribution. By means of the programme, the distribution curve is in a constant state of being updated, the samples reducing exponentially in significance in relation to the samples taken subsequent to them. The most recent readings are thus the most significant whilst older readings are less significant and eventually become completely insignificant. The theoretical probability of a given reading occurring can be calculated, or conversely a given probability of a signal level occurring will correspond to a specific signal level. Thus the alarm level may be continually re-set for a given probability of occurring. In the instance of one sample being taken every second, if the level is set to correspond to 1 chance in $10^6$, then, in theory, an unwanted alarm would be generated on average once every 115 days from normal fluctuations of the signal level. If it is set at 1 in $10^7$, an unwanted alarm would be generated on average once every 3 years. The probability of this signal level occurring five times in a row will be once every 243 years. Such a method provides the means for setting the alarm level with a given theoretical probability of an unwanted alarm occurring. Also the mean level of signal is known from the assumed normal distribution and any fall in this below what can be expected may indicate a fault in the detector head 19.

Figure 9:
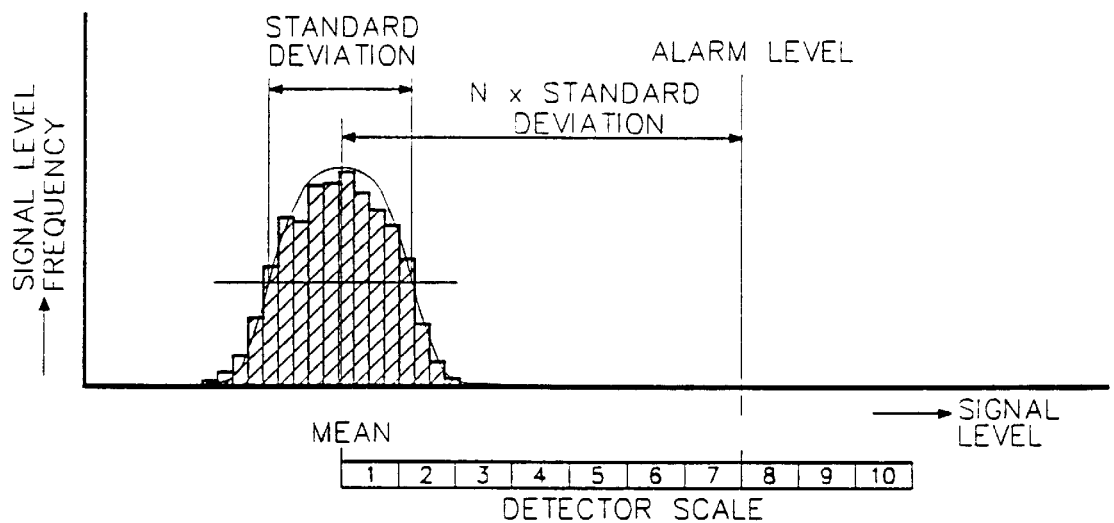
FIG. 9 shows a diagram of a typical signal histogram and distribution curve illustrating processing of a signal from the detector head by the electrical functions of FIG. 7, with the amplitude of a smoke signal being plotted on the X-axis and frequency of occurrence of such smoke signal being plotted on the Y-axis.

The updating of the distribution curve is achieved as follows. The detector sensitivity range as referred to herein is defined as the signal levels which occur between two adjustably set limits. Sampled signal levels are allocated to selected ones of a number of classes covering the range. The classes have limits related to signal levels which define the class width such that a number of classes will occur within the range and be contiguous. No reading within the range will fail to be allocated to a class. The classes may be all equal in width or each class have a width in relation to its position within the range. Every class consists of an identical number range which has a maximum value of any convenient value and a minimum value of zero. When a sample signal is received, the class to which it corresponds is incremented by an amount which is a fraction of the difference between the present and the maximum values of that class; all other classes are decremented by the same fraction of their difference from zero. The fraction of increment and decrement is hereinafter called the Entry Constant. In starting-up the apparatus, after a number of samples, which is dependent upon the Entry Constant, and which is taken over a relatively short period, for example 20 minutes, the class entries will approach a true representation of the distribution curve of their levels across the range. Once a distribution curve has been fully established, the Entry Constant may be decreased. By variation of the Entry Constant the time period for which the entries are of practical significance can be set anywhere between minutes and days, but normally set at 3 to 4 hours. The mean of the readings and the standard deviation of the readings in the ordinary state of the volume being sampled are used to calculate an alarm level. The calculation of alarm level is made to give a theoretical probability of an unwanted alarm occurring. FIG. 9 shows a typical signal histogram and distribution curve resulting from this procedure.

The method of deriving the histogram results in one that shows a distribution weighted in favour of the most recent additions. Also the entries are normalised such that the total area of the histogram remains constant and represents 100% of the qualifying entries. The method of changing the present values of the classes is such that the class in which an entry is made will be increased while all other classes in the histogram will be simultaneously decreased. The amount of increase will be exponentially towards a common and arbitrarily set maximum representing 100%. The amount of decrease will be exponentially towards zero. Consider the entries made in just one class after a number of entries in the total histogram have been made. Its proportion to the 100% level will be approaching the proportion of the number of entries made in that class to the total number of entries. Also there will be an exponentially decreasing emphasis on entries made earlier. Each class can be seen to be approaching a level between its maximum and zero which represents the proportion of entries made recently in that class.

FIGS. 10A, B and C show imagined histograms that may be obtained by the method described. The X-axis is the same scale for each of the three diagrams, as is the Y-axis. Histogram 'A' is intended to represent the distribution that will result from a very pure air sample. In this case the distribution is entirely due to the electrical noise generated by the detector board 39 and the detector head 19. This histogram would correspond to a 'Filter Renew Fault'. Histogram 'B' is intended to represent an averagely dirty sample. The increased width of the curve will result in a lower peak to it. Histogram 'C' further illustrates the fall in the peak due to a further increase in width. This is imagined to be due to the detector head 19 taking a dirtier sample.

Referring again to FIG. 9, a bargraph will be set such that bargraph level 8 is equivalent to the alarm level. It will be noted that the zero for the bargraph is set at the mean of the distribution. The histogram only needs to cover the levels 0 to 2 (or possibly 3 for very dirty environments).

The alarm level will be set to have a fixed probability of occurring. A pre-alarm level will be programmable to any level between 5 and 7 (inclusive). An auxiliary level (for example for automatic closure of fire doors or for automatic shutting-down of equipment) will be programmable to any level between 4 and 10 (inclusive). In order for any of these levels to be activated, a programmable number of consecutive entries must be made in or above the corresponding class. The number of consecutive entries will not be allowed to be less than two. Since entries are to be made at fixed time intervals, the number of consecutive entries required will constitute a time delay. Because these delays are customer programmable, there is no way of predetermining how they may be programmed. This requires the ability to handle the situation where an alarm can be activated before the pre-alarm. This situation cannot be allowed. It can be prevented by either automatically bringing on the pre-alarm if the alarm is activated or not allowing an alarm to be activated until the pre-alarm has been activated. A third possibility is that the alarm condition cannot begin to be determined (i.e. number of consecutive entries) until the pre-alarm is activated. The first of these possibilities will give the most rapid response to a fire and the third will give the slowest response.

The present method includes fault detection which is performed as follows. The most likely fault to occur with the filter is that it will become overloaded with the residue from the filtrate. The effect of this will be to increase the efficiency of the filter so that it will remove smaller and smaller particles from the filtrate (the "tea leaf effect"). This becomes dangerous for a smoke detector when the particle size is so low that it filters out smoke. If it is assumed that all environments contain a small amount of smoke (or similar suspension), the absence of the signal which this generates can be detected. Although the above assumption is not universally true, it is generally true. In the cases where it is not true (e.g., clean rooms, computer rooms etc.,), the air is very clean and consequently the filter is unlikely to become over-loaded in a short time. A general practice of changing the filter once a year should easily cope with such conditions. The system can cope with this situation by using a real time clock to generate a filter renew signal at yearly intervals.

Figure 11:
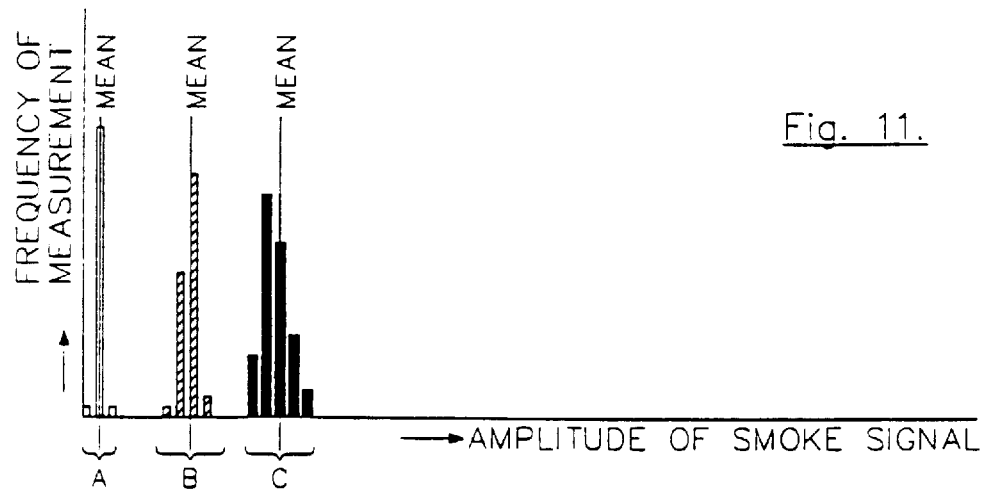
FIG. 11 is a diagram similar to FIG. 9, but illustrating the histograms for various states of an air filter.

Referring to FIG. 11, detection of the filter fault is performed by the continuous statistical analysis of the signal from the detector head 19, whereby the mean level and the standard deviation are derived. When no smoke signal is present then these will normally be at low levels, as indicated by the histogram C in FIG. 11. The micro-processor 45 detects when they have fallen to an abnormally low level, as indicated by the histogram B in FIG. 11, between the histogram C and the histogram A representing pure air and generates a "filter renew" signal.

There are two types of fault which may affect the sensor 28. There may be an absence of signal (due to broken connections or component failure) or there may be a change in scale or offset (due to component deterioration with age or environmental conditions).

The easiest method of detecting the absence of signal is similar to that for detecting a filter fault. If it is used, then care is taken to differentiate between the two causes. The absence of signal will give a lower mean and standard deviation than a blocked filter.

The change in scaling is immaterial to the processing, which sets the controlling scale according to the signal it is receiving. However, if the scale of the detector head 19 is continuously deteriorating, there will come a point where the microprocessor 45 is setting the alarm level either in the region where the natural noise in the electronics could cause an alarm or above where the detector head 19 is capable of generating a signal. Since the controlling scale is generated so that an alarm condition corresponds to bargraph 8, a mechanism is built into the microprocessor procedure to disallow the alarm level to be set below an absolute level or above the capabilities of the detector head 19. This will limit the deterioration in the detector head scale which the microprocessor can handle. When this mechanism is about to be called into operation, then a "head fault" is generated.

Figure 12:
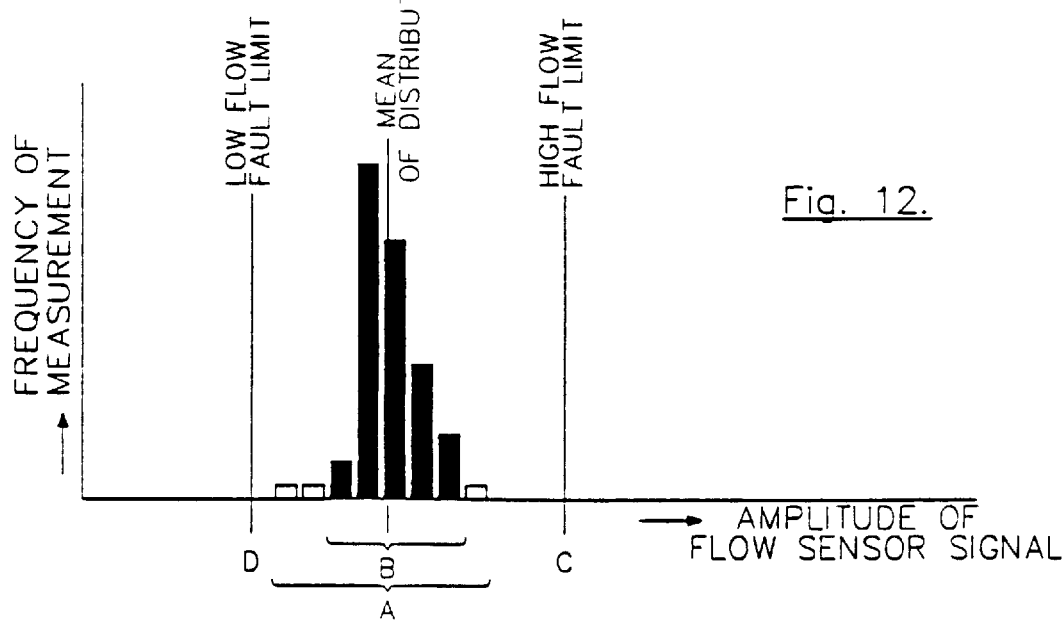
FIG. 12 is a diagram of a typical signal histogram illustrating processing of a signal from the air-speed transducer by electrical functions of FIG. 7, with the amplitude of the air-speed signal being plotted along the X-axis and the frequency of occurrence of such signal being plotted along the Y-axis.

Referring to FIG. 12, another fault is an air speed fault which is determined by a microprocessor function with a very long time duration. This function will generate a histogram of air speeds sensed by the transducer 20. The high speed and low speed limits C and D are programmable with respect to the mean. The number of classes should be a minimum (say eight) in order to save on memory space. The class range and position are under software control but not automatically set during the normal functioning of the system. They may only be set automatically and when in the programming mode and when requested. When so requested, the present reading of the air speed monitoring transducer 20 will be assumed to be the mean and the class range A will extend from 50% to 150% of this mean. This does not mean that the fault limits cannot be set outside this range. It does mean that, in normal operation, the majority of the readings will be inside the range, as indicated at B.

Figure 14:
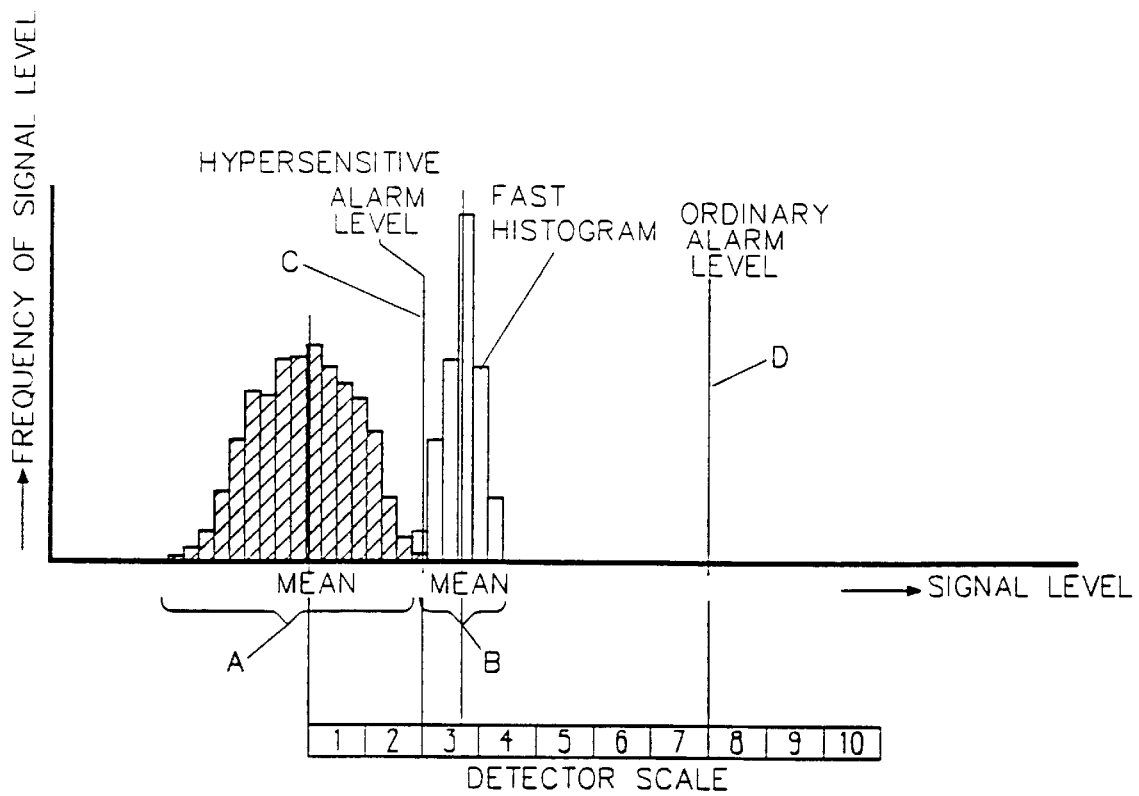
FIG. 14 is a diagram similar to FIG. 9, but illustrating the relationship among an "ordinary" signal histogram and alarm level, a fast histogram and a hypersensitive alarm level.

The hyper-sensitive mode is an option wherein a centre of distribution of the amplitude of the detector head output signals changes to an abnormally high value and whereby a reliable alarm signal will be generated at levels that would ordinarily have a high probability of false alarm. This mode is not necessarily an alternative to the ordinary mode of generating an alarm but may be an extension of it, i.e. the ordinary mode may exist beside it. The ordinary processing maintains a distribution curve (A in FIG. 14) of the background signal levels which the detector head 19 has detected over the last 3 to 4 hours. Another distribution curve (B in FIG. 14) is maintained which does exactly the same but over the last 10 to 15 minutes. Any small change will immediately become apparent by comparing the two. The hyper-sensitive mode will detect these changes and signal an alarm when the change exceeds a given limit. The limit must be set high enough to avoid any variations in distribution that may occur ordinarily. Even allowing for this, an alarm level (C in FIG. 14) can be set well inside the ordinary probable false alarm region of the system and well below the alarm level (D in FIG. 14) that would be used in the ordinary mode. Although the hyper-sensitive mode takes 10–15 minutes to respond, it will detect the slow build-up stage of a standard fire before the ordinary mode. Also it will detect small sources of heat which will never become a full-scale fire. In FIG. 14, an alarm condition for the hypersensitive mode is shown.

Since the background signal levels are being used to set the alarm level there is a possible difficulty with the preferred method. This is apparent when considering the rapid variations of environment which will naturally occur (these rapid variations are only a difficulty if their maximum rates of change are greater than the microprocessor's rate of learning, which is a programmable function). For instance there is the difference in background signal levels which occurs when an office block, or other work space, comes into use in the morning compared with when it goes out of use in the evening. During the daytime it will automatically set the alarm level high and at night it will automatically set it low. However, at the start of the day it will be some time before it raises the alarm level because it takes time to learn about the new conditions. During this time the system will have the level set too low. Similarly, in the evening it takes time to set the alarm level low and during this time it will be set too high.

Figure 13:
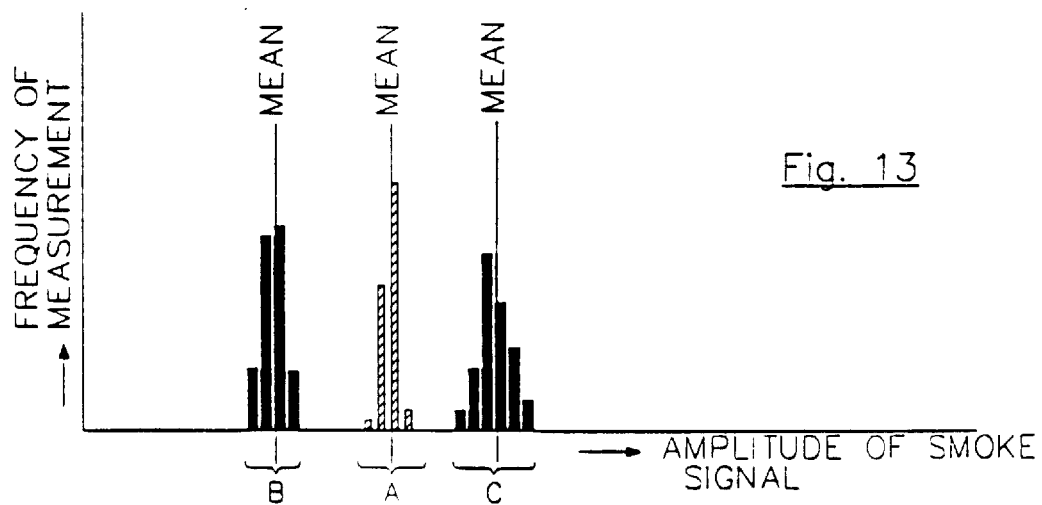
FIG. 13 is a diagram similar to FIG. 9, but illustrating the relationships among a "night" histogram, a "day" histogram and a "fast" histogram.

There are a number of ways in which this difficulty can be overcome. Except for one, they all depend upon having two sets of analysis data; one for the "day" conditions and another for the "night" conditions. These data are the histograms accumulated during the day (C in FIG. 13) and during the night (B in FIG. 13). The different ways of dealing with the difficulty concern how to switch from one to the other. The simplest method is to use the real time clock and programme in the "day" and "night" commencement times. This is cumbersome and far from foolproof since someone may enter the premises at night time or there may be a day off when the premises are unoccupied. An alternative is to have a day/night switch which the last person out switches to "night" and the first person in switches to "day". This is very similar to the normal burglar alarm. Another alternative is to make it automatic by having a fast learning histogram (A in FIG. 13) which can be produced in, say, 10 to 15 minutes and which detects the increase and decrease in activity and operates the day/night switch. The hyper-sensitive mode is only used In ultraclean environments where the difference between the "day" and "night" conditions is minimal, in which case the day/night switch would not be needed at all. Another method which does not depend upon keeping two sets of data, i.e. the "day" and "night" histograms, would use a fast learn mode. In this mode the system could be told to learn, say, in 30 minutes instead of 3 hours during only the transition period between "day" and "night". Any of the above methods could be used to initiate the transition period.

The automatic switching from "day" to "night" data by detecting the rise and fall of activity is the most foolproof method but would require that the hypersensitive mode illustrated in FIG. 14 could not be used in conjunction with it. Since it is unlikely that the two would be required together, there is no great problem.

Figure 15:
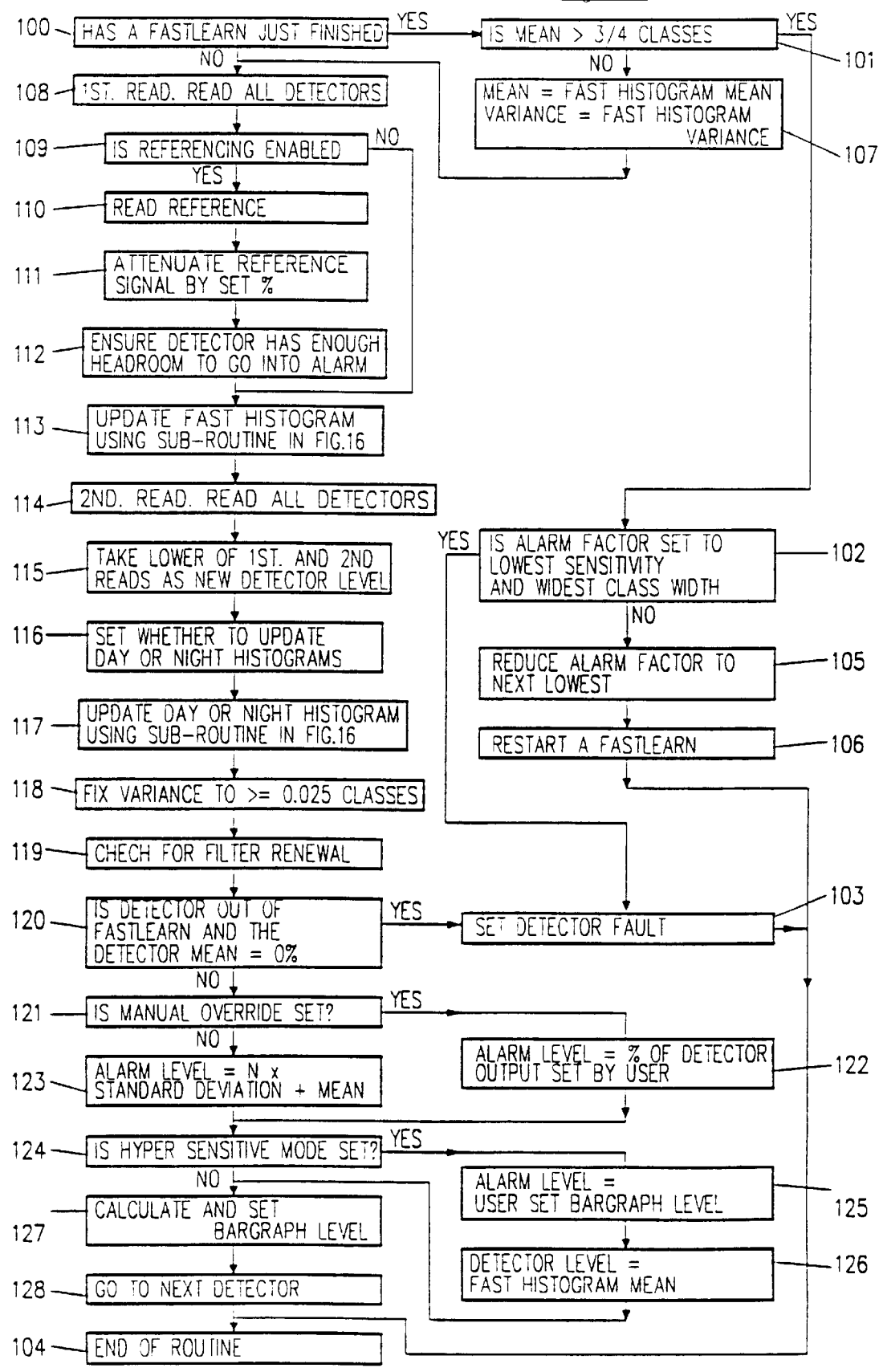
FIG. 15 illustrates a software routine, for use in a microprocessor of FIG. 7, of reading detectors and calculating alarm levels.
Figure 16:
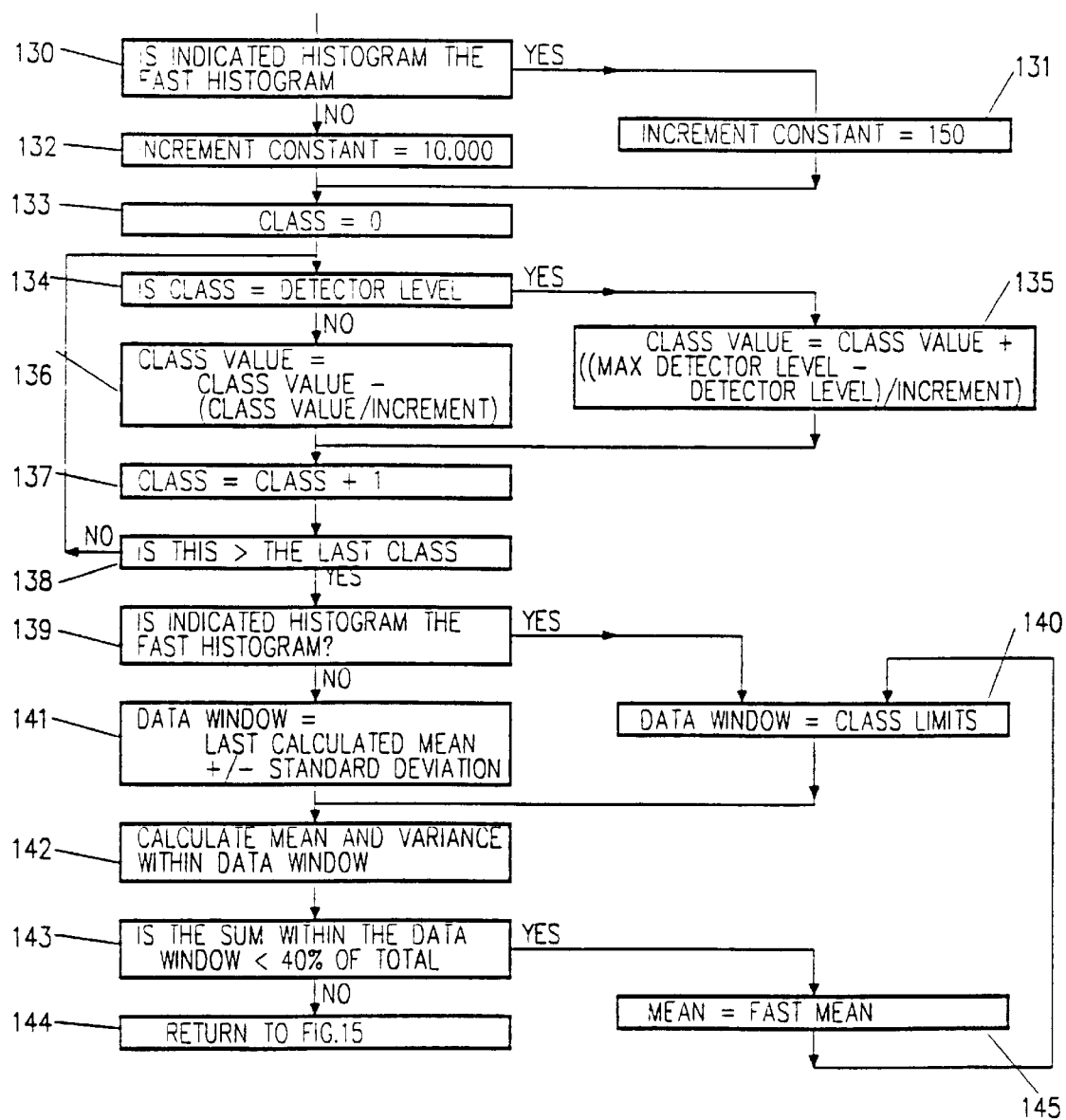
FIG. 16 shows a software sub-routine called from the routine of FIG. 15, the sub-routine being of incrementing and decrementing classes and of calculating means and variances.

The software routine of FIG. 15 and its subroutine of FIG. 16 are contained in the ROM 47. The routine of FIG. 15 and its sub-routine of FIG. 16 are cycled through for every reading of a detector head. The first instruction 100 is as to whether a fast-learn mode has just finished; if the answer is "yes" the second instruction 101 is to ask whether the calculated mean of the histogram established falls within the highest 25% of the classes in the detector sensitivity range. If the answer is "yes" the next instruction 102 is to ask whether the alarm factor (the specific, adjustable, preset probability of a false alarm occurring) is set to the lowest sensitivity, corresponding to the greatest permissible class width in the detector sensitivity range. If the answer is "yes", then the final instruction 103 is to set a detector fault and proceed to the end 104 of the routine. If the answer to instruction 102 is "no", the next instruction 105 is to reduce the alarm factor to the next lowest sensitivity, corresponding to the next greatest class width, followed by an instruction 106 to restart the fast-learn mode, and then proceed to end 104. If the answer to instruction 101 is "no", then the next instruction 107 is to set the mean to the fast histogram mean and the variance to the fast histogram variance. This, or an answer "no" to instruction 100, is followed by an instruction 108 to carry out a first reading of the outputs of all of the smoke detector heads. The next instruction 109 is to ask whether referencing, i.e. the reference detector head, is enabled. If the answer is "yes" the next instruction 110 is to read the reference detector head output. The following instruction 111 is to attenuate the reference output signal by a set percentage. This is set by the user and takes account of the normal circumstances that the smoke content measured by the reference detector head may not all enter the protected volume. The next instruction 112 is to ensure that the reference output signal is not so great in relation to the voltage range of the detection module that the detection module has enough head room to provide an alarm level signal. The next instruction 113, which is also proceeded directly to if the answer to the instruction 109 is "no", is to update the fast histogram, for example A in FIG. 13 using the sub-routine of FIG. 16. The next instruction 114 is to take a second reading for all detection modules. The following instruction 115 is to take the lower of the first and second readings as the new reading for the current detection module (i.e. the detection module currently being read). Then, there is the instruction 116 to decide whether the new reading is to be entered into the "day" or "night" histogram (such as C or B in FIG. 13). The next instruction 117 is to update the relevant histogram using the sub-routine of FIG. 16. The following instruction 118 is, if the variance falls within 2.5% of the classes in the detector sensitivity range, to accept for future calculation a variance which is not less than 2.5% of the classes in the detector sensitivity range.

The following instruction 119 is to check whether filter renewal is required, owing to the mean of the histogram falling (as indicated at B in FIG. 11) by a pre-set percentage from the mean of the histogram obtained with a new filter such as the histogram C in FIG. 11). The next instruction 120 is to ask whether the detection module is out of the fast-learn mode and the mean of the detection histogram equals zero percent. If the answer is "yes" then the instruction 103 is given. If the answer is "no" then the next instruction 121 is to ask whether a manual override is set, whereby alarm levels have been manually set. If the answer is "yes" then the instruction 122 is to set the alarm level to be equal to the detection output percentage set by the user. If the answer is "no", then the instruction 123 is to set the alarm level at n (see FIG. 9) times the standard deviation plus the mean. The instruction following instruction 122 or 123, as the case may be, is to ask whether the hypersensitive mode has been set; if the answer is "yes" the next instruction 125 is to set the alarm level at the bargraph level set by the user. Then the next instruction 126 is to enter the detection output reading as the fast histogram mean. This instruction 126, or the instruction 124 if its answer is "no", is followed by the instruction 127 to calculate and set the detection reading entered on the bargraph level. The following instruction 128 is to proceed to the next detection module, whence end 104 follows.

Referring to FIG. 16, when the sub-routine shown therein is called, a first variable indicating which detection module and a second variable indicating which histogram, are sent. The first instruction 130 is to ask as to whether the indicated histogram is the fast histogram; if the answer is "yes" then an instruction 131 to set an increment constant (equal to the inverse of the Entry Constant) at 150 follows. If the answer is "no" then an instruction 132 to set an increment constant of 10,000 follows. Following the instruction 131 or 132, as the case may be, is an instruction 133 to set a variable called "class" equal to zero. The next group of instructions 134 to 138 constitutes a loop. The first instruction 134 of these is to ask whether the detection output level falls within the current "class". If the answer is "yes", then the instruction 135 is to set the new class frequency value equal to the current class frequency value plus the difference between the maximum detection frequency level and the current detection frequency level, divided by the increment constant. If the answer is "no", then the instruction 136 is to set the new class frequency value equal to the current class frequency value minus the current class frequency value divided by the increment constant. After instruction 135 or 136, as the case may be, the instruction 137 is to set the "class" equal to the current class plus one, and this is followed by the instruction 138 asking whether this latter is greater than the last permissible class in the detector sensitivity range. If the answer is "no", the loop is repeated, whereas, if the answer is "yes" the next instruction 139 is to ask whether the indicated histogram is the fast histogram. If the answer is "yes" then the instruction 140 is to set a data window equal to the detector sensitivity range. If the answer is "no" the instruction 141 follows to set the data window as the last calculated mean plus or minus the standard deviation. Following the instruction 140 or 141, as the case may be, is the instruction 142 to calculate the mean and the variance for those classes within the data window. The next instruction 143 is to ask whether the sum of the frequencies within the data window is less than 40% of the sum of all the frequencies within the detector sensitivity range. If the answer is "no", the next instruction 144 is to return to the relevant originating step in FIG. 15. If the answer is "yes", then the instruction 145 is to set the mean equal to the fast histogram mean and is followed by the instruction 140.

We claim:

1. A method of detecting the content of impurity in a gaseous medium, comprising continually statistically analysing signals which are emitted by detecting means detecting said impurity and which vary with variation in said content, characterised in that, in the statistical analysis, newer signals are accorded greater influence on outputs than are older signals, which become gradually less influential.

2. A method according to claim 1, wherein, in said statistical analysis, said newer signals are sorted into a plurality of classes into which the older signals have already been sorted, and the entry in each class into which such newer signal is sorted is incremented by an amount dependent upon the existing entry in that class and the entries in the classes into which such newer signal is not sorted are decremented by amounts dependent upon the respective existing entries in those classes.

3. A method according to claim 1, wherein a warning indication is produced if and when amplitude of said signals passes an abnormal threshold.

4. A method according to claim 3, wherein said statistical analysis is performed to set said abnormal threshold.

5. A method according to claim 4, wherein the statistical analysis is performed to establish said threshold at a predetermined multiplier times the standard deviation of the distribution of the signals.

6. A method according to claim 2, wherein the statistical analysis is performed to establish a centre of distribution of the signals as an assumed ordinary value of said signals.

7. A method according to claim 6, wherein said warning indication is produced if and when said centre of distribution passes said threshold.

8. A method according to claim 2, wherein a bargraph is established the zero of which is a centre of distribution of said signals.

9. A method according to claim 6, wherein said centre of distribution is a mode, a median, or a mean.

10. A method according to claim 2, wherein said statistical analysis is performed to compare distribution curve constants of the signals during a first time period with the same distribution curve constants of the signals during a second time period different from the first time period.

11. A method according to claim 2, and further comprising selecting from between an ordinary mode and a fast mode of establishing the distribution of said signals.

12. A method according to claim 1, wherein the detecting of the impurity is performed by emitting a beam of radiation from radiation-emitting means, causing said gaseous medium to flow through a focus region of said beam, and reflecting radiation scattered from said beam to radiation-sensing means disposed in the region of said radiation-emitting means.

13. A method according to claim 12, wherein said gaseous medium is caused to flow through an inlet of a housing containing said radiation-emitting means, said radiation-sensing means and said focus region and is so guided in said housing that all of the gaseous medium entering said housing passes through said focus region.

14. A method according to claim 12, wherein said gaseous medium is caused to flow generally longitudinally of said beam.

15. A method according to claim 1, wherein the detecting of the impurity is performed in a secondary duct means through which flows only part of a stream of said gaseous medium flowing through main duct means.

16. A method according to claim 15, wherein said part is a central part of said stream.

17. A method according to claim 1, and further comprising detecting the speed of flow of said gaseous medium by passing the medium over an electrically heated sensor, thereby tending to cool said sensor from a desired temperature, increasing the electrical power dissipated in said sensor to counterbalance the cooling tendency, and measuring the increase in the electrical power dissipated.

18. A method according to claim 17, and further comprising obtaining reference temperature signals from a reference sensor in the flow of said gaseous medium and adjacent said electrically heated sensor, and using said reference temperature signals as reference for the electrical power measurements.

19. A method according to claim 18, wherein the temperature in the electrically-heated sensor is continuously maintained at a predetermined difference above the temperature in the reference sensor.

20. A method according to claim 19, wherein said difference is no more than several degrees Kelvin.

21. Apparatus for detecting the content of impurity in a gaseous medium, comprising detecting means serving to detect said impurity, analysing means serving continually to analyse statistically signals which are emitted by said detecting means and which vary with variation in said content, said analysing means comprising numerically calculating means, characterised in that said numerically calculating means continually performs a statistical analysis in which newer data inputs are accorded greater influence on the outputs than are older data inputs, which become gradually less influential.

22. Apparatus according to claim 21, wherein, in said statistical analysis, said newer signals are sorted into a plurality of classes into which the older signals have already been sorted, and the entry in each class into which such newer signal is sorted is incremented by an amount dependent upon the existing entry in that class and the entries in the classes into which such newer signal is not sorted are decremented by amounts dependent upon the respective existing entries in those classes.

23. Apparatus according to claim 21, and further comprising warning-producing means serving to produce a warning indication if and when amplitude of the signals passes an abnormal threshold.

24. Apparatus according to claim 21, including a master which comprises said detecting means, said analysing means, signal output means, and electrical supply means electrically connected to said analysing means and said signal output means, and a slave which comprises other detecting means and which is electrically connected to said analysing means, said signal output means and said electrical supply means.

25. Apparatus according to claim 24, wherein said master and said slave comprise respective modules.

26. Apparatus according to claim 24, wherein said slave comprises reference detecting means.

27. Apparatus according to claim 25, wherein said master and said slave comprise respective detection modules.

28. Apparatus according to claim 27, and further comprising a second slave which comprises further detecting means and which is electrically connected to said analysing means, said signal output means and said electrical supply means, said second slave comprising a reference module.

29. Apparatus according to claim 25, wherein each module has associated therewith a back box in which are terminations of electrical supply lines and gaseous medium supply ducting and into which the electrical supply lines and gaseous medium ducts of the module can be plugged.

30. Apparatus according to claim 21, and further comprising an interface whereby a personal computer can be connected to said analysing means for data transmission therebetween.

31. Apparatus according to claim 21, wherein said detecting means comprises a detector head for detecting impurity in a gaseous medium, comprising a housing, an inlet of said housing for entry of said gaseous medium carrying said impurity, radiation-emitting means for emitting a beam of radiation to pass through said medium and focussed to a first location in said housing, radiation-reflective means disposed opposite said radiation-emitting means and encircling said location for focussing radiation scattered from said beam by said impurity to a second location in the region of said radiation-emitting means, and radiation-sensing means disposed at said second location for sensing the radiation focussed thereto by said radiation-reflective means.

32. Apparatus according to claim 31, wherein the arrangement is such that said gaseous medium is guided to flow generally longitudinally of said beam.

33. Apparatus according to claim 32, wherein inlet and outlet holes for said gaseous medium are formed through the wall of said housing substantially co-axially with said beam.

34. Apparatus according to claim 31, wherein there is substantially no gap between said radiation-reflective means and said housing through which said gaseous medium can flow, whereby said gaseous medium is caused to flow through a central hole through said radiation-reflective means.

35. Apparatus according to claim 21, and further comprising main duct means through which a stream of said gaseous medium can flow, and secondary duct means containing said detecting means and communicating with said main duct means for receiving only part of said stream.

36. Apparatus according to claim 35, wherein said secondary duct means extends along and in said main duct means.

37. Apparatus according to claim 21, and further comprising speed-detecting means for detecting speed of flow of said gaseous medium, said speed-detecting means comprising an electrically heatable sensor, electrical power supply means connected to said sensor for heating the sensor, control means connected to said supply means and said sensor and serving to cause increase of electrical power dissipated in said sensor to counterbalance cooling of said sensor, and measuring means serving to measure said increase of electrical power dissipated.

38. Apparatus according to claim 37, wherein said sensor is electrically connected in series with a resistor.

39. Apparatus according to claim 38, wherein electrical control circuit means supplies current to a junction between said sensor and said resistor to control current through said sensor.

40. Apparatus according to claim 37, and further comprising a reference sensor adjacent said electrically heated sensor and electrical circuitry connected to the sensors and wherein reference temperature signals obtained from the reference sensor are used as reference for the electrical power measurements.

41. Apparatus according to claim 40 wherein said electrically heated sensor is electrically connected in series with a resistor, and wherein the reference sensor is electrically connected in series with a second resistor whereof the resistance is at least several times greater than that of the other resistor.

42. A data processing method utilizing numerical calculation, wherein a statistical analysis is continually performed in which newer data inputs are accorded greater influence on the outputs than are older data inputs, which become gradually less influential, characterised by sorting said newer data inputs into a plurality of classes into which the older data inputs have already been sorted, and incrementing the entry in each class into which such newer data input is sorted by an amount dependent upon the existing entry in that class and decrementing the entries in the classes into which such newer data input is not sorted by amounts dependent upon the respective existing entries in those classes.

43. A method according to claim 42, and further comprising setting an abnormal threshold for said data inputs.

44. A method according to claim 43, wherein said statistical analysis is performed to set said abnormal threshold.

45. A method according to claim 44, wherein the statistical analysis is performed to establish said threshold at a predetermined multiplier times the standard deviation of the distribution of the data inputs.

46. A method according to claim 42, wherein the statistical analysis is performed to establish a centre of distribution of the data inputs as an assumed ordinary value thereof.

47. A method according to claim 46 and further comprising setting an abnormal threshold for said data inputs, said centre of distribution being able to pass said threshold.

48. A method according to claim 42, wherein a bargraph is established the zero whereof is a centre of distribution of the data inputs.

49. A method according to claim 46, wherein said centre of distribution is a mode, a median, or a mean.

50. A method according to claim 42, wherein said statistical analysis is performed to compare distribution curve constants of the data inputs during a first time period with the same distribution curve constants of the data inputs during a second time period different from the first time period.

51. A method according to claim 42, and further comprising selecting from between an ordinary mode and a fast mode of establishing the distribution of said data inputs.

52. Data processing apparatus incorporating numerically calculating means such that a statistical analysis can be continually performed in which newer data inputs are accorded greater influence on the outputs than are older data inputs, which become gradually less influential, characterised in that said calculating means sorts said newer data inputs into a plurality of classes into which said calculating means has already sorted the older data inputs, and in that said calculating means increments the entry in each class into which such newer data input is sorted by an amount dependent upon the existing entry in that class and decrements the entries in the classes into which such newer data input is not sorted by amounts dependent upon the respective existing entries in those classes.

53. A method of detecting the content of impurity in a gaseous medium, comprising receiving signals which are emitted by detecting means detecting said impurity and which vary with variation in said content, producing a warning indication if and when amplitude of the signals passes an abnormal threshold corresponding to an abnormal content of said impurity, and continually statistically analysing the received signals to set said abnormal threshold.

54. A method according to claim 53, wherein the statistical analysis is performed to establish said threshold at a predetermined multiplier times the standard deviation of the distribution of the signals.

55. A method according to claim 53, wherein the statistical analysis is performed to establish a centre of distribution of the signals as an assumed ordinary value of said signals.

56. A method according to claim 55, wherein the statistical analysis is performed to establish said threshold at a predetermined multiplier times the standard deviation of the distribution of the signals, and wherein said warning indication is produced if and when said centre of distribution passes said threshold.

57. Apparatus for detecting the content of impurity in a gaseous medium, comprising detecting means serving to detect said impurity, receiving means serving to receive signals which are emitted by said detecting means and which vary with variation in said content, warning-producing means serving to produce a warning indication if and when amplitude of the signal passes an abnormal threshold corresponding to an abnormal content of said impurity, and continually statistically analysing means interposed between said receiving means and said warning producing means and which continually statistically analyse the received signals to set said abnormal threshold.

58. A method of detecting the content of impurity in a gaseous medium, comprising receiving signals which are emitted by detecting means detecting said impurity and which vary with variation in said content, and producing a warning indication if and when amplitude of the signals passes an abnormal threshold, characterised by continually statistically analysing the received signals to ascertain when a centre of distribution of amplitude of the signals passes said threshold and producing said warning indication accordingly.

59. A method according to claim 58, wherein a bargraph is established the zero of which is a centre of distribution of said signals.

60. A method according to claim 58, wherein said centre of distribution is a mode, a median, or a mean.

61. Apparatus for detecting the content of impurity in a gaseous medium, comprising detecting means serving to detect said impurity, receiving means serving to receive signals which are emitted by said detecting means and which vary with variation in said content, and warning-producing means serving to produce a warning indication if and when amplitude of the signals passes an abnormal threshold, characterised by continually statistically analysing means interposed between said receiving means and said warning-producing means and which continually statistically analyse the received signals to ascertain when a centre of distribution of amplitude of the signals passes said abnormal threshold.

62. A detector for detecting impurity in a gaseous medium, comprising a housing, an inlet of said housing for entry of said gaseous medium carrying said impurity, radiation-emitting means for emitting a beam of radiation to pass through said medium and focussed to a first location in said housing, radiation-reflective means for focussing radiation scattered from said beam by said impurity to a second location in said housing, and radiation-sensing means disposed at said second location for sensing the radiation focussed thereto by said radiation-reflective means, characterized in that said radiation-reflective means is disposed opposite said radiation-emitting means and is annular and encircles said first location, and in that said second location is in the region of said radiation-emitting means.

63. A detector according to claim 62, wherein the arrangement is such that said gaseous medium is guided to flow generally longitudinally of said beam.

64. A detector according to claim 63, wherein inlet and outlet holes for said gaseous medium are formed through the wall of said housing substantially co-axially with said beam.

65. A detector according to claim 62, wherein there is substantially no gap between said radiation-reflective means and said housing through which said gaseous medium can flow, whereby said gaseous medium is caused to flow through a central hole through said radiation-reflective means.

66. A method of detecting the content of impurity in a stream of gaseous medium flowing through main duct means, comprising by causing only part of said stream to flow into secondary duct means and through a filter disposed in said secondary duct means and then detecting the content of the impurity in the gaseous medium in said secondary duct means.

67. A method according to claim 66, wherein said part is a cross-sectionally central part of said stream.

68. Apparatus for detecting the content of impurity in a stream of gaseous medium, comprising main duct means through which said stream can flow, secondary duct means communicating with said main duct means for receiving only part of said stream, a filter disposed in said secondary duct means, and detecting means downstream of said filter and serving to detect the content of the impurity in the gaseous medium in said secondary duct means.

69. Apparatus according to claim 68, wherein said secondary duct means extends along and in said main duct means.

70. A detector according to claim 62, further comprising:
 a light trap for said beam, said light trap located behind said radiation-reflective means.

* * * * *